United States Patent [19]
Tomalski et al.

[11] Patent Number: 5,854,002
[45] Date of Patent: Dec. 29, 1998

[54] METHOD OF IDENTIFYING COMPOUNDS THAT BIND TO THE INSECT GABA RECEPTOR

[75] Inventors: Michael D. Tomalski, Raleigh; Daniel B. Gant, Durham, both of N.C.

[73] Assignee: Rhone Poulenc, Inc., Research Triangle Park, N.C.

[21] Appl. No.: 768,301

[22] Filed: Dec. 17, 1996

[51] Int. Cl.$^6$ ............... G01N 33/566; C07K 14/435; C12N 5/10; C12N 15/63

[52] U.S. Cl. ............ 435/7.2; 435/325; 435/348; 435/320.1; 435/252.3; 435/254.11; 435/69.1; 530/350

[58] Field of Search ............ 435/7.2, 325, 348, 435/69.1, 252.3, 254.11, 320.1; 530/350

[56] References Cited

U.S. PATENT DOCUMENTS 5,487,976  1/1996  Soderlund et al. ............ 435/7.21

OTHER PUBLICATIONS

Zhang et al., Subunit composition determines picrotoxin and bicuculline sensitivity of Drosophila gamma–aminobutyric acid receptors, Mol. Pharmacol., 48(5):835–40, Nov. 1995.

Lee et al., Expression of a Drosophila GABA receptor in a baculovirus insect cell system. Functional expression of insecticide susceptible and resistant GABA receptors from the cyclodiene resistance gene Rdl, FEBS Lett., 335(3): 315–318, 1993.

Bloomquist (1996) *Annu. Rev. Entomol.* 41:163.

Ffrench–Constant et al. (1991) *Proc. Nat'l Acad. Sci. USA* 88:7209.

Ffrench–Constant et al. (1993) *Nature* 363:449.

Harvey et al. (1994) *J. Neurochem.* 62:2480.

Henderson et al. (1993) *Biochem. Biophys. Res. Commun.* 193:474.

Lunt et al. (1985) *Neurochem. Int.* 7:751.

Millar et al. (1994) *Proc. R. Soc. Lond.* 258:307.

*Primary Examiner*—Stephen Walsh
*Assistant Examiner*—Claire M. Kaufman
*Attorney, Agent, or Firm*—Baker & Botts LLP

[57] ABSTRACT

The present invention provides a method of measuring the ability of a compound to bind to the GABA recognition site of an insect GABA receptor. The invention further provides host cells that express a nucleic acid encoding the GABA receptor subunit LCCH3 and a nucleic acid encoding the GABA receptor subunit Grd, and cell membranes obtained from the host cells.

26 Claims, 12 Drawing Sheets

METHOD OF IDENTIFYING COMPOUNDS THAT BIND TO THE INSECT GABA RECEPTOR

FIELD OF THE INVENTION

Insect γ-aminobutyric acid (GABA)-gated chloride channels are the site of action for a number of insecticides, including for example the cyclodienes. Another class of insecticidal compounds, the phenylpyrazoles, have recently been found to act on the GABA receptor at a site that appears to be slightly different than the cyclodiene site of action. Thus the GABA receptor is a viable target for the discovery of new and more efficacious insecticides. The present invention provides a method of identifying compounds that interact at the GABA recognition site on the insect GABA receptor.

BACKGROUND OF THE INVENTION

GABA is the predominant inhibitory amino acid neurotransmitter which acts, via $GABA_A$-type receptors, to inhibit synaptic transmission in both vertebrate and invertebrate nervous systems. When two molecules of GABA bind at sites on the receptor, a channel opens allowing chloride ions to flow passively down the electrochemical gradient into the neuron. An influx of chloride into the cell causes a change in the membrane potential, usually a hyperpolarization, which results in an inhibition of the nerve impulse.

$GABA_A$-type receptors contain a diversity of binding sites for a number of pharmaceutically important drugs in mammals and for pesticides in insects. GABA receptors in insects are activated by GABA and muscimol, are generally bicuculline-insensitive, and are blocked by picrotoxin, cyclodiene insecticides (e.g. dieldrin), phenylpyrazole insecticides (e.g. Fipronil®), bicyclophosphorous esters (e.g. t-butylbicyclophosphorothionate (TBPS)), and bicycloorthobenzoates (e.g. 4-n-propyl-4'-ethynylbicycloorthobenzoate (EBOB)). Compounds that interact with the insect GABA-gated chloride channel and disrupt its proper function have been found to be useful as insecticides (Bloomquist (1996) *Annu. Rev. Entomol.* 41:163; Bloomquist et al. (1992) *Pestic. Sci.* 32: 463, Buckingham et al. (1994) *Neurosci. Lett.* 181:137; Casida (1993) *Arch. Insect Biochem. Physiol.* 22:13; Cole et al. (1993) *Pest. Biochem. Physiol.* 46:47; Deng et al. (1993) *Pest. Biochem. Physiol.* 47:98.

Much more is known about the $GABA_A$ receptors from vertebrates than from insects. Vertebrate receptors are composed of heterooligomeric, membrane-spanning glycoproteins which are believed to consist of five subunit proteins: two α's, two β's, and one γ. Multiple subunits have been derived from vertebrates, including α1-6, β1-3, γ1-3, δ1, and ρ1-2. Combinations of these subunits, specifically the α's, β's and γ's, associate in cells to form a number of functional $GABA_A$ receptors having distinct pharmacologies and neurological distributions. For reviews see McKernan et al. (1996) *TINS* 19:139; Conley, *The Ion Channel FactsBook I: Extracellular Ligand-Gated Channels* (Academic Press, New York, 1996), and Tyndale, R. F. et al., "Ligand-and voltage-gated ion channels", in *Handbook of Receptors and Channels* (R. A. North, ed., CRC Press, Inc., 1995).

By comparison, only three classes of GABA receptor subunit genes have been derived from insects. These have been designated as 1) resistance to dieldrin (Rdl) (ffrench-Constant et al. (1991) *Proc. Natl. Acad. Sci. USA* 88:7209); 2) glycine-like receptor from Drosophila (Grd) (Harvey et al. (1994) *J. Neurochem.* 62:2480); and 3) ligand-gated chloride channel homologue 3 (LCCH3 or the β-like subunit) (Henderson et al. (1993) *Biochem. Biophys. Res. Comm.* 193:474). Initially, the products of these genes were categorized as GABA receptors based on their high amino acid sequence homology to that of the vertebrate GABA receptors.

Of the three classes of insect GABA receptor subunit genes, only Rdl was found to form receptors that exhibited the functional characteristics of GABA-gated chloride channels. When expressed in oocyte and insect cells in vitro, and analyzed by electrophysiology and patch-clamp techniques, these homo-oligomers exhibited membrane depolarization in response to GABA and the GABA agonist, muscimol, and the block of the GABA response by picrotoxin (ffrench-Constant et al. (1993) *Nature* 363:449). In addition, an insect cell line expressing homo-oligomeric Rdl receptors was found to specifically bind [$^3$H]muscimol (Millar et al. (1994) *Proc. R. Soc. Lond. B.* 258:307). Little is known about channels formed from the expression of combinations of Grd and/or LCCH3 with Rdl. Zhang et al. (1995) *Molec. Pharm.* 48:835 report that the in vitro expression of Rdl and LCCH3 combinations produces two distinctive receptor types: Rdl homomultimers which are picrotoxin sensitive but bicuculline insensitive, and Rdl plus LCCH3 heteromultimers which are picrotoxin insensitive but bicuculline sensitive. Since the pharmacology of Rdl homomultimers is most like that of cultured larval neurons, Zhang et al. concluded that LCCH3 does not contribute to the formation of the most abundant GABA receptor found in vivo. In addition, at the amino acid level, LCCH3 and Grd exhibit only 26% and 34% identity overall, respectively, to Rdl. Therefore, the roles of Rdl, Grd and LCCH3 in the in vivo composition and assembly of GABA-gated chloride channels in insects are unclear.

Cell lines expressing GABA receptor subunits that exhibit the pharmacology of native insect GABA receptors are of interest in understanding the role of the various subunit genes, and for the identification of compounds that interact with the insect GABA receptor.

The present invention addresses the need for the identification of new and more efficacious insecticides by providing host cells that express that GABA receptor subunit genes. The host cells are useful for the identification of compounds that interact with the insect GABA receptor.

SUMMARY OF THE INVENTION

The present invention provides host cells that express a nucleic acid encoding the insect GABA receptor subunit Grd and a nucleic acid encoding the insect GABA receptor subunit LCCH3.

The present invention further provides host cells containing a vector comprising a nucleic acid encoding Grd under the control of a promoter and a vector comprising a nucleic acid encoding LCCH3 under the control of a promoter.

In another embodiment, the present invention is directed to a baculovirus expression vector comprising a nucleic acid encoding Grd, and a baculovirus expression vector comprising a nucleic acid encoding LCCH3.

The present invention also provides kits and compositions comprising cell membranes wherein the membranes comprise the insect GABA receptor subunits Grd and LCCH3.

Another aspect of the present invention provides a method of measuring the ability of a compound to bind to the GABA recognition site of an insect GABA receptor, wherein the GABA receptor comprises Grd and LCCH3 subunits.

DETAILED DESCRIPTION OF THE INVENTION

Figure 1:
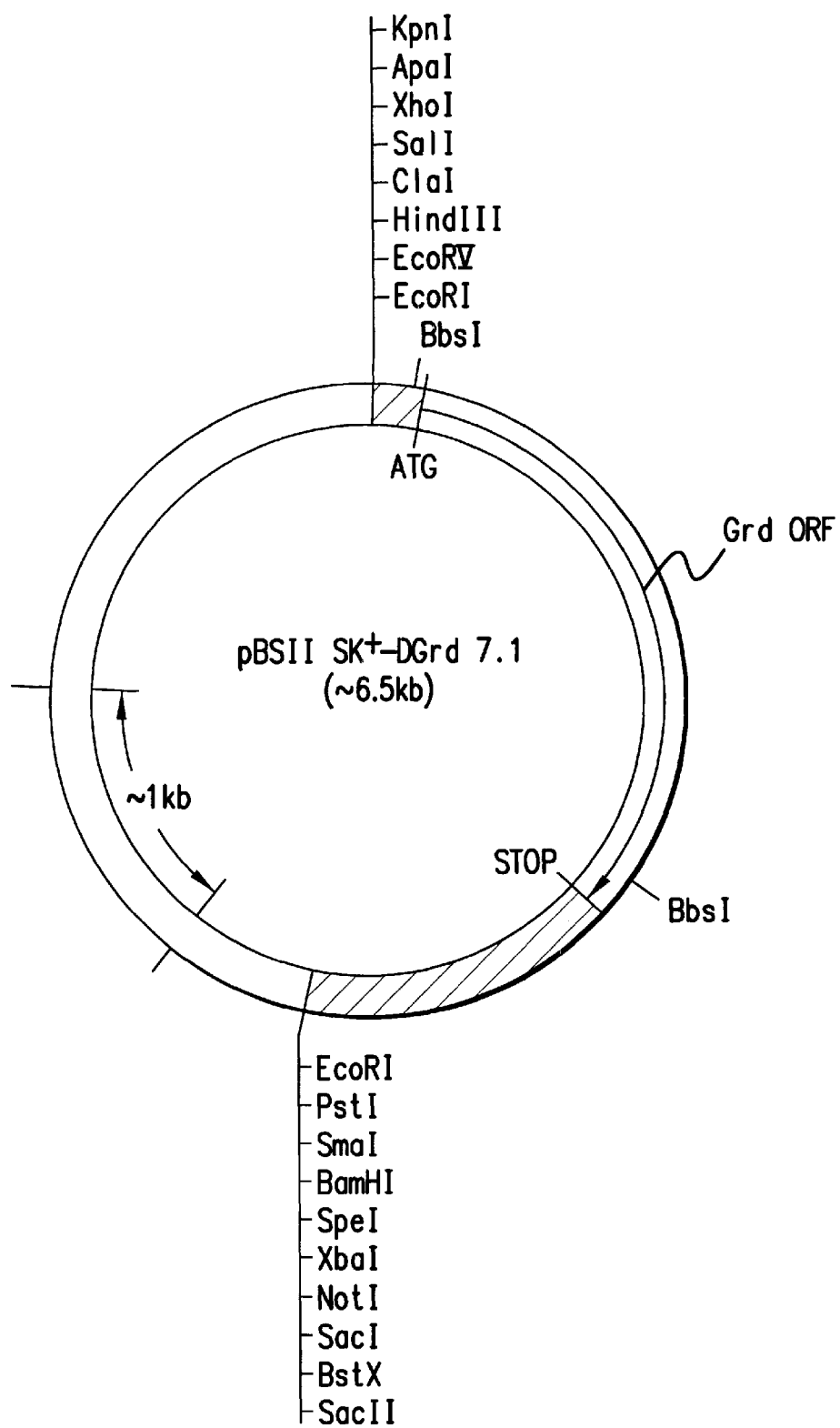
FIG. 1 depicts the plasmid pBSIISK$^+$-DGrd7.1.

The present invention provides host cells that express nucleic acids encoding the insect GABA receptor subunits LCCH3 and Grd. The co-expression of the subunits results in the formation of a GABA-recognition site in the host cell membrane. A GABA-recognition site is defined herein as a binding site of a protein or polypeptide that specifically binds GABA or the radiolabeled GABA agonist, [$^3$H] Muscimol, or other ligands which bind to the GABA recognition site with high affinity. The present invention further provides a method of making and using the host cells, and in particular a method of identifying compounds that bind to the GABA-recognition site of the insect GABA receptor.

In one embodiment, the present invention provides an expression vector comprising a nucleic acid encoding LCCH3, and an expression vector comprising a nucleic acid encoding Grd.

In one embodiment of the present invention, the nucleic acid encoding LCCH3 is a DNA molecule having the sequence disclosed by Henderson et al., *Biochem. Biophys. Res. Comm.* 193:474–482, 1993 and set forth herein as SEQ ID NO:1. In another preferred embodiment, the nucleic acid encoding LCCH3 has a nucleotide sequence that encodes the amino acid sequence of SEQ ID NO:2. Those of ordinary skill in the art, with the knowledge of the degeneracy of the genetic code, can determine nucleotide sequences that encode the amino acid sequence of SEQ ID NO:2.

In one embodiment of the present invention, the nucleic acid encoding Grd is a DNA molecule having the nucleotide sequence available from GENEBANK and set forth herein as SEQ ID NO:3. In another preferred embodiment, the nucleic acid encoding Grd has a nucleotide sequence that encodes the amino acid sequence of SEQ ID NO:4. The amino acid sequence of SEQ ID NO:4 is disclosed by Harvey et al. (1994) *J.Neurochem.* 62:2480. The ordinarily skilled artisan, with the knowledge of the degeneracy of the genetic code, can determine nucleotide sequences that encode the amino acid sequence of SEQ ID NO:4.

Those of ordinary skill in the art are aware that minor modifications of the foregoing sequences can be tolerated while maintaining the function of the nucleic acid, i.e. the ability to encode LCCH3 or Grd. For example, a nucleotide sequence can be selected to optimize expression in a particular host organism by utilizing known preferred condons for the host organism of choice. As used herein, the terms "nucleic acid encoding LCCH3" and "nucleic acid encoding Grd" encompass nucleic acids having the sequences set forth above as well as variants thereof including for example fragments, deletions, insertions and substitutions that maintain the ability to encode LCCH3 and Grd. In particular, those of ordinary skill in the art can determine acceptable modifications that do not affect the GABA-recognition site formed by the co-expression of the LCCH3 and Grd subunit nucleic acids in accordance with the present invention. Nucleic acids encoding Grd and LCCH3 include those nucleic acids which, when co-expressed in an insect host cell such as *Trichoplusia ni*, result in the formation of GABA recognition sites in the host cell membrane that exhibit specific binding for [$^3$H] muscimol of at least about 40%, and more preferably of at least above 85%, and a $K_d$ of from about 10 to about 40 nM.

The present invention provides expression vectors comprising nucleic acids encoding LCCH3 and capable of expressing the LCCH3 subunit in a suitable host cell. The invention further provides expression vectors comprising nucleic acids encoding Grd and capable of expressing the Grd subunit in a suitable host cell. A single vector comprising a nucleic acid encoding LCCH3 and a nucleic acid encoding Grd and capable of expressing both subunits in a suitable host cell is also provided.

In the vectors of the present invention, the nucleic acid encoding LCCH3 or Grd is operably linked to suitable transcriptional and/or translational regulatory elements to effect expression of the LCCH3 or Grd subunit in a suitable host cell. The regulatory elements may be derived from mammalian, microbial, viral or insect genes and include, for example, promoters, enhancers, transcription and translation initiation sequences, termination sequences, origins of replication, and leader and transport sequences. Suitable regulatory elements are selected for optimal expression in a desired host cell.

Expression vectors can be constructed by well known molecular biological methods as described for example in Sambrook et al. (1989) *Molecular Cloning: A Laboratory Manual* Cold Spring Harbor Laboratory Press, Cold Spring Harbor, N.Y., or any of a myriad of laboratory manuals on recombinant DNA technology that are widely available. Expression vectors into which the nucleic acids of the present invention can be cloned under the control of a suitable promoter are also commercially available. Recombinant viral vectors, including retroviral, baculoviral, parvoviral and densoviral vectors are particularly preferred. In host cells containing vectors having an inducible promoter controlling the expression of the nucleic acid encoding LCCH3 or Grd, expression is induced by methods known in the art and suitable for the selected promoter. For example, expression of nucleic acids under the control of the metallothionein promoter is induced by adding cadmium chloride or copper sulfate to the growth media of host cells.

In a preferred embodiment the expression vector comprises a strong constitutive or inducible promoter operably linked to a nucleic acid encoding LCCH3 or Grd. Suitable promoters are well known and readily available to those of ordinary skill in the art, and include for example, the heat shock promoter, metallothionein promoter, dexamethasone promoter, alcohol dehydrogenase promoter, and the baculovirus promoters, i.e., the early promoter (e.g., IE-1 and etl), the late promoters (e.g., vp39 and p6.9), the very late promoters (e.g., polh and p10) and the hybrid promoter (e.g., vp39/polh).

Another embodiment of the present invention provides a host cells containing a vector comprising a nucleic acid encoding Grd under the control of a promoter and a vector comprising a nucleic acid encoding of LCCH3 under the control of a promoter. The host cell may be procaryotic or eukaryotic, including bacterial, yeast, insect and mammalian cells. Insect and mammalian cells are preferred. Particularly preferred host cells include insect cell lines, including for example *Spodoptera frugiperda* and *Trichoplusia ni* cells. The host cells may be transformed, transfected or infected with the expression vectors of the present invention by methods well-known to those of ordinary skill in the art. Transfection may be accomplished by known methods, such as liposome mediated transfection, calcium phosphate mediated transfection, microinjection and electroporation. Permanently transformed insect cell lines are particularly preferred. In a preferred embodiment, insect cell lines such as Drosophila Schneider Line 1 (SL1) cells are permanently transformed by co-transfection with an expression vector comprising a nucleic acid encoding LCCH3 and an expression vector comprising a nucleic acid encoding Grd. In a preferred embodiment the expression vectors are baculovirus expression vectors, and transfection of SL1 cells is preformed by the lipofectin procedure described by O'Reilly et al., *Baculovirus Expression Vectors: A Laboratory Manual*, W. M. Freeman & Co., New York, 1992, incorporated herein by reference.

Expression systems utilizing baculovirus vectors and insect host cells are provided in accordance with the present invention. In particular, the present invention provides a baculovirus expression vector comprising a nucleic acid encoding LCCH3, and a baculovirus expression vector comprising a nucleic acid encoding Grd. Baculovirus expression vectors comprising a nucleic acid encoding LCCH3 and a nucleic acid encoding Grd are also contemplated herein. The use of baculoviruses as recombinant expression vectors to infect insect host cells is known in the art and described for example by O'Reilley et al. (1992), Luckow et al. (1988) *Bio/Technology* 6: 47 and Miller (1988) *Ann. Rev. Microbiol.* 42:177, the disclosures of which are incorporated herein by reference. The baculovirus vectors generally contain a strong baculovirus promoter operably linked to a nucleic acid encoding LCCH3 or Grd such that the promoter directs expression of LCCH3 or Grd. Baculovirus polyhedrin promoters such as the *Autographa californica* nuclear polyhedrosis virus polyhedrin promoter are preferred.

The baculovirus expression vectors of the present invention are made by inserting the nucleic acid encoding LCCH3 or Grd downstream of the polyhedrin promoter in a baculovirus transfer vector, for example pBacPac8 available from CLONTECH Laboratories, Inc., 1020 East Meadow Circle, Palo Alto, Calif. 94303. Baculovirus transfer vectors further contain flanking baculovirus sequences that allow homologous recombination between the transfer vector and baculovirus DNA during co-transfection. The transfer vector containing the nucleic acid of the invention and viral DNA are used to co-transfect insect cells. In a preferred embodiment the insect cells are Spodoptera. *Spodoptera frugiperda* cells including Sf9 are particularly contemplated. During co-transfection, homologous recombination results in the transfer of an expression cassette containing the polyhedrin promoter and the nucleic acid of the present invention to the polyhedrin locus of the viral DNA. The resulting recombinant virus is used to generate viral stocks by standard methods. Insect host cells are infected with the recombinant virus to produce insect cells expressing LCCH3 and Grd.

Figure 10:
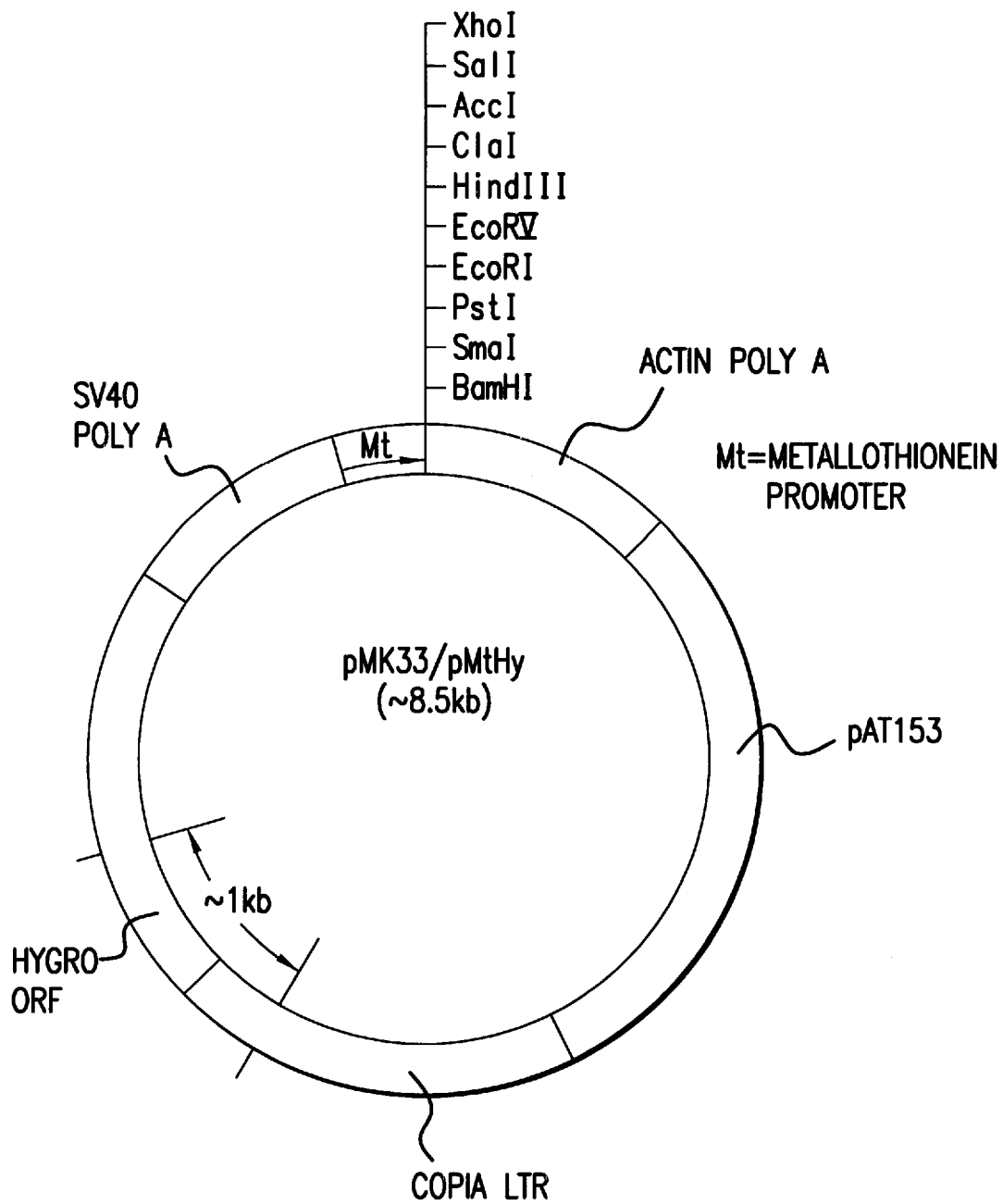
FIG. 10 depicts the plasmid pMK33/pMtHy.

Insect host cells that are preferred for the production of permanently transformed host cells that express Grd and LCCH3 include, for example, SL1 and SL2 cells. Preferred expression vectors for the production of the permanently transformed cell lines include transformation vectors that express dominant selectable markers such as antibiotic resistance. In a preferred embodiment, the plasmid vector is pMK33/pMtHy depicted in FIG. 10. The vector pMK33/pMtHy contains the *Drosophila metallothionein* (Mt) promoter preceded by a multiple cloning site for the insertion of a nucleic acid encoding LCCH3 or Grd, and a hygromycin resistance gene under the control of the copia LTR promoter. The hygromycin resistance gene provides a marker that allows selection of stably transformed cell lines carrying the plasmid. A detailed description of the construction of the pMK33/pMtHy plasmid is provided by Krasnow et al. (1989) *Cell* 57:1031 and Kaufman et al. (1989) *Cell* 59:359, the disclosures of which are incorporated herein by reference.

Insertion of the nucleic acid encoding LCCH3 or the nucleic acid encoding Grd into the multiple cloning site of a vector such as pMK33/pMtHy results in the production of an expression vector containing a nucleic acid encoding LCCH3 or Grd under the control of the Mt promoter. Insect host cells are co-transfected with the vector encoding LCCH3 and the vector encoding Grd, for example, by the lipofection procedure described by O'Reilly et al. (1992) supra. Transformed insect host cells maybe identified by selection with tissue culture media supplemented with the antibiotic to which resistance is conferred by the vector, e.g. hygromycin. Clonal colonies are then isolated and amplified. Because these vectors contain the inducible Mt promoter, the expression of the LCCH3 and Grd proteins is induced by adding cadmium chloride to the growth medium.

The host cells of the present invention express, or are induced to express, a nucleic acid encoding LCCH3 and a nucleic acid encoding Grd. In accordance with the present invention it has been discovered that co-expression of the insect GABA receptor LCCH3 and Grd subunits in the host cell results in the formation of an LCCH3/Grd multimer having a GABA-recognition site in the cell membranes of the host cells. The presence of a GABA-recognition site is determined by the ability of the host cell or membranes of the host cell to specifically bind [$^3$H] muscimol, a radiolabeled GABA agonist.

The LCCH3/Grd multimer formed by the co-expression of the nucleic acid encoding LCCH3 and the nucleic acid encoding Grd in a host cell is referred to herein as an insect GABA receptor comprising LCCH3 and Grd subunits. It has been discovered in accordance with the present invention that the insect GABA receptor of the invention has a GABA-recognition site that exhibits pharmacology that is very similar to the sites of native insect GABA receptors, for example from housefly heads, as described by Lunt et al. (1985) *Neurochem. Int.* 7:751. In particular, the host cells of the present invention that co-express the nucleic acids encoding LCCH3 and Grd, and cell membranes derived from the host cells, specifically bind the GABA agonist [$^3$H] muscimol. In contrast, host cells that express only the nucleic acid encoding LCCH3, or only the nucleic acid encoding Grd, fail to exhibit specific [$^3$H] muscimol binding. Specific binding is defined as saturatable [$^3$H] muscimol binding of high affinity. In the [$^3$H] muscimol LCCH3/Grd assay, specific binding for [$^3$H] muscimol is defined as binding of at least about 50%, under standard assay conditions such as those described below.

Accordingly, the host cells of the present invention, and membranes derived therefrom, are useful for determining the ability of compounds to bind to the GABA recognition site of an insect GABA receptor. Agents that bind to the GABA recognition site of an insect GABA receptor are well-known to be useful as insecticides, as discussed hereinabove.

Accordingly, the present invention provides a method of measuring the ability of a compound to bind to the GABA recognition site of an insect GABA receptor, wherein the receptor comprises the Grd and LCCH3 subunits. The host cells that co-express nucleic acids encoding LCCH3 and Grd or preferably membranes or membrane fragments obtained from the host cells, are subjected to a radioligand binding assay utilizing [$^3$H] muscimol, [$^3$H] GABA, or other ligands which bind to the GABA recognition site. The host cells or membranes are incubated in a suitable buffer with an amount of [$^3$H] muscimol capable of being fully bound to the host cells or membranes, and with varied known amounts of a compound to be tested for its ability to bind to the GABA recognition site. The incubation is terminated, radioactivity that is not bound to the cells or membranes is separated from radioactivity that remains bound, and the amount of radioactivity that remains bound to the cells or membranes is determined.

If the test compound has the ability to bind to the GABA recognition site, a portion of the [$^3$H] muscimol that would bind to the membrane is competitively or non-competitively displaced and thus separable from the membrane. Thus, the amount of radioactivity that remains bound is proportional to the ability of the test compound to bind to the GABA recognition site.

In particular, the present method comprises the steps of: incubating, in an aqueous solution, a known amount of host cells that express a nucleic acid encoding the LCCH3 subunit and a nucleic acid encoding the Grd subunit, or membranes obtained from the host cells, and [$^3$H]-muscimol in a known amount capable of binding to the known amount of host cells or membranes, and varied known amounts of a compound to be tested for its ability to bind to the GABA recognition site for a time and under conditions suitable for a portion of said [$^3$H]-muscimol to bind to said host cells or membranes;

separating the cells or membranes from the [$^3$H]-muscimol that is not bound to the cells or membranes;

determining the GABA receptor binding activity of said compound.

Either intact cells or membranes containing insect GABA receptors comprising LCCH3 and Grd subunits may be used in the present method. Membranes can be obtained from the host cells of the present invention by methods known in the art. In a representative method, the host cells that express Grd and LCCH3 are pelleted by centrifugation, and the pellets are frozen, for example at −80° C. The frozen pellet is then thawed, suspended in buffer, and gently homogenized, for example by about five strokes in a glass/Teflon homogenizer. Membranes are then pelleted one or more times by centrifugation, for example at 120,000 g for 30 minutes. The membrane pellet is resuspended in buffer, for example 10 mM phosphate buffer pH 7.4. The protein concentration of the membranes may be determined by methods known to those of ordinary skill in the art. The membrane suspensions may be frozen for later use.

The host cells of the invention or membranes derived therefrom may be contained in any suitable vessel to perform the method of the present invention. Suitable vessels include for example, glass test tubes, polystyrene test tubes, and microtiter plates. For example, by using 96 well microtiter plates, multiple test compounds can be assayed simultaneously, and thus the present method can be used to provide a high throughput screen to identify potential insecticidal compounds.

For the radioligand binding assay of the invention, the host cells or membranes are combined in an aqueous solution with [$^3$H]muscimol and the test compound. The aqueous solution may be a physiological buffer such as a saline solution including for example phosphate buffered saline, tris (hydroxymethyl) aminomethane (TRIS) or N-[2-Hydroxyethyl] piperazine-N-[2-ethanesulfonic acid] (HEPES). The [$^3$H] muscimol is used in an amount capable of being fully bound to the amount of intact cells or membranes used in the assay. The ordinarily skilled artisan can determine the amount of [$^3$H] muscimol that is bound to a particular amount of cells or membranes by determining standard dose-response curves as described for example by Limbird, Cell Surface Receptors: A Short Course on Theory and Methods, Martinus Nijhoff Publishing, Boston, 1986. For example, it has been determined herein that a final concentration of 5–10 nM [$^3$H]muscimol is suitable for use with a membrane preparation having a protein content of about 125 $\mu$g.

The test compound is used in a known amount, and multiple assays are performed with varied known amounts in order to obtain a dose-response curve. A control assay is performed in which test compound is replaced by buffer. In a preferred embodiment, the test compound is used at a concentration of from about 1 nM to about 100 $\mu$M. Those of ordinary skill in the art can determine suitable and convenient volumes of the components of the assay. For example, a convenient assay may be performed using 200 $\mu$L of membrane preparation containing 125 $\mu$g of protein, 100 $\mu$L of the 50 nM [$^3$H] muscimol, 20 $\mu$L of test compound, and 680 $\mu$L of buffer.

The intact cells or membranes, [$^3$H]muscimol and test compound are incubated for a time and under conditions suitable to achieve binding of [$^3$H] muscimol to the GABA-recognition site in the intact cells or membranes. In a preferred embodiment, the incubation is conducted for 45 to 180 minutes at from 30° C. to 4° C., respectively. In a more preferred embodiment, the incubation is conducted for about 90 minutes at about 4° C.

The incubation is terminated by separating the cells or membranes from the aqueous solution in which the incubation was conducted. In a preferred embodiment the termination is accomplished by vacuum filtration on glass fiber filters followed by washing of filters with cold buffer.

The GABA receptor binding activity of the test compound is proportional to the amount of [$^3$H]muscimol that is separated from the cells or membranes. The amount of [$^3$H] muscimol that is separated is determined by measuring the radioactivity bound to the cells or membranes retained on the filter. The amount of radioactivity that is separated is compared to the amount of radioactivity that is separated when the same assay is conducted in the absence of test compound. Radioactivity may be measured by methods known in the art, for example by liquid scintillation spectrometry.

Radioactivity measurements are used to determine radioligand binding parameters such as $K_D$ and $IC_{50}$ which are, in turn, determined by kinetic and equilibrium analysis of saturation binding data (Limbird, 1986) supra. $K_D$ is the equilibrium dissociation constant which represents the concentration of ligand that half-maximally occupies the receptor at equilibrium. $IC_{50}$ is the molar concentration of the test compound needed to produce half-maximal displacement of

[³H] muscimol from a GABA receptor comprising the LCCH3 and Grd subunits. The $IC_{50}$ provides a direct measure of the ability of the test compound to bind to the GABA recognition site of the insect GABA receptor of the invention. Compounds having $IC_{50}$ values of about 100 μM or less in the method of the present invention are considered to interact with the GABA recognition site of the insect GABA receptor comprising LCCH3 and Grd subunits.

Compounds identified as capable of interacting with the GABA recognition site may be useful as insecticides. Compounds identified by the present method may be assessed for insecticidal activity by in vitro and in vivo methods known in the art.

The present invention further provides compositions useful in the practice of the method of the invention. In one embodiment, the invention provides a composition comprising cell membranes containing the insect GABA receptor subunits Grd and LCCH3. In a preferred embodiment the cell membranes are insect cell membranes. The cell membranes may be prepared as described hereinabove. Membranes containing the Grd and LCCH3 subunits are capable of specifically binding [³H] muscimol and thus are useful in the methods of the present invention. The compositions may further comprise an aqueous solution such as a physiological buffer. Suitable physiological buffers include, for example, PBS, TRIS and HEPES.

The present invention further provides a kit for measuring the ability of compounds to bind to the GABA recognition site of an insect GABA receptor. The kit contains a first container containing a host cell expressing or capable of expressing a nucleic acid encoding LCCH3 and a nucleic acid encoding Grd. In another embodiment the kit contains a first container containing a cell membrane comprising an LCCH3 subunit and a Grd subunit. The membrane may be in the form of a membrane preparation, including a freeze dried membrane preparation, or may be contained in intact cells. In a preferred embodiment, the cells are insect cells and the membranes are derived from insect cells.

The following examples further illustrate the present invention.

EXAMPLE 1

Expression of the cDNAs Encoding the Insect GABA Receptor Subunit Homologues, LCCH3, Grd and Rdl, in the Baculovirus Expression System All procedures in this and the following examples, including cell culture, transfection, isolation, purification, characterization and propagation of viruses, and expression, electrophoresis and visualization of infected cell proteins, are standard methods described in O'Reilly et al., *Baculovirus Expression Vectors: A Laboratory Manual*, W. H. Freeman & Co., New York 1992, the disclosure of which is incorporated herein by reference.

Figure 2:
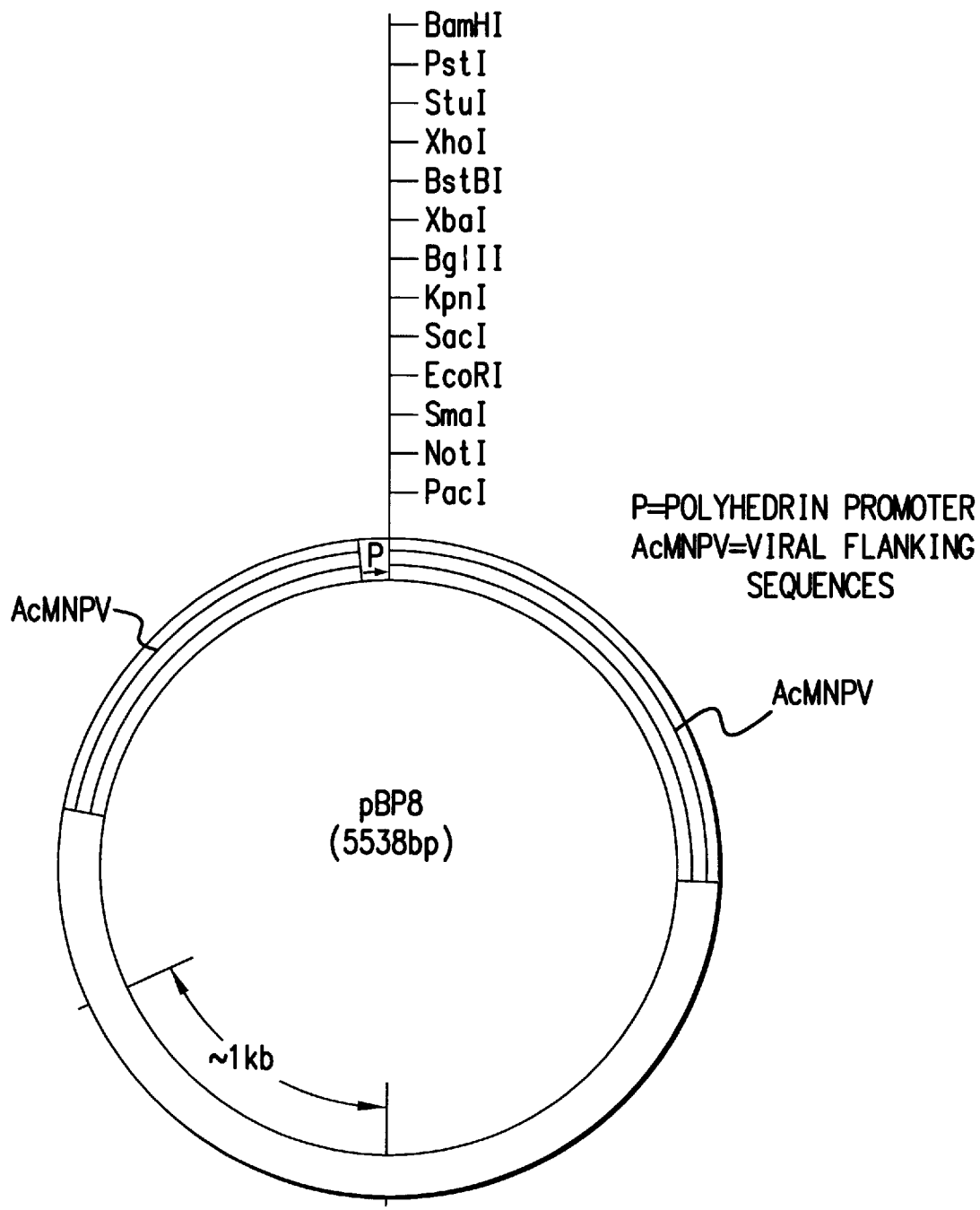
FIG. 2 depicts the plasmid pBP8.
Figure 3:
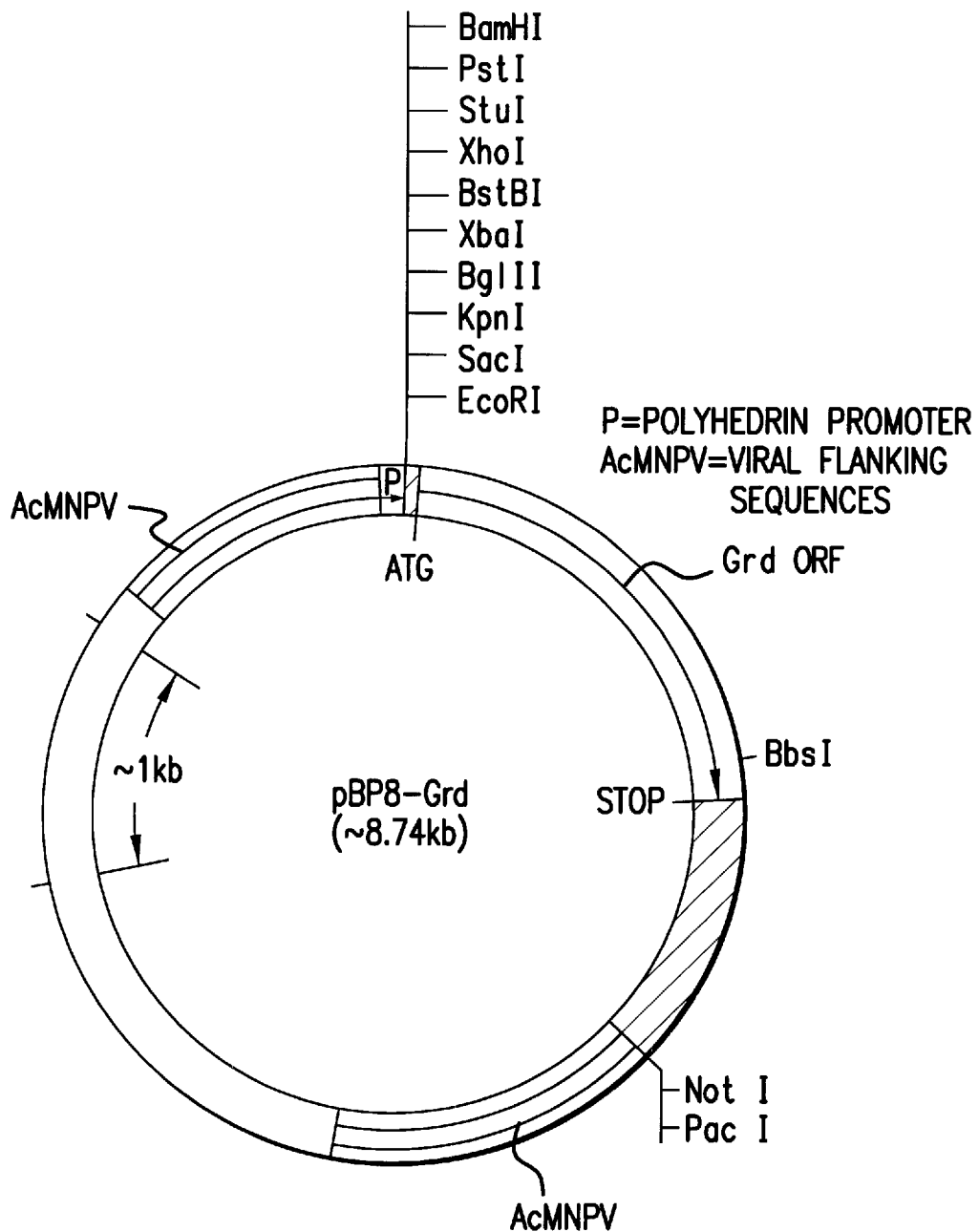
FIG. 3 depicts the plasmid pBP8-Grd.

The plasmid pBP8-Grd was constructed as follows. A 3.2 kb blunt-ended BbsI/blunt-ended EcoRI DNA fragment, containing the complete coding sequence of Grd, was excised from the plasmid, pBSIISK⁺-DGrd7.1. The plasmid PBSIISK⁺-Grd 7.1 is disclosed by Harvey et al. (1994) *J. Neurochem.* 62:2480 and depicted in FIG. 1. This fragment was cloned into the SmaI site of the baculovirus transfer vector pBacPAK8 (CLONTECH Laboratories, Inc.) (FIG. 2) to produce the 8.7 kb plasmid, pBP8-Grd (FIG. 3), which contains Grd under the control of the very strong polyhedrin promoter and flanked on either side by 1,250 bp and 1,433 bp of viral sequence, respectively. Restriction enzyme mapping was used to confirm the correct insertion of the Grd cDNA in pBP8-Grd.

Figure 4:
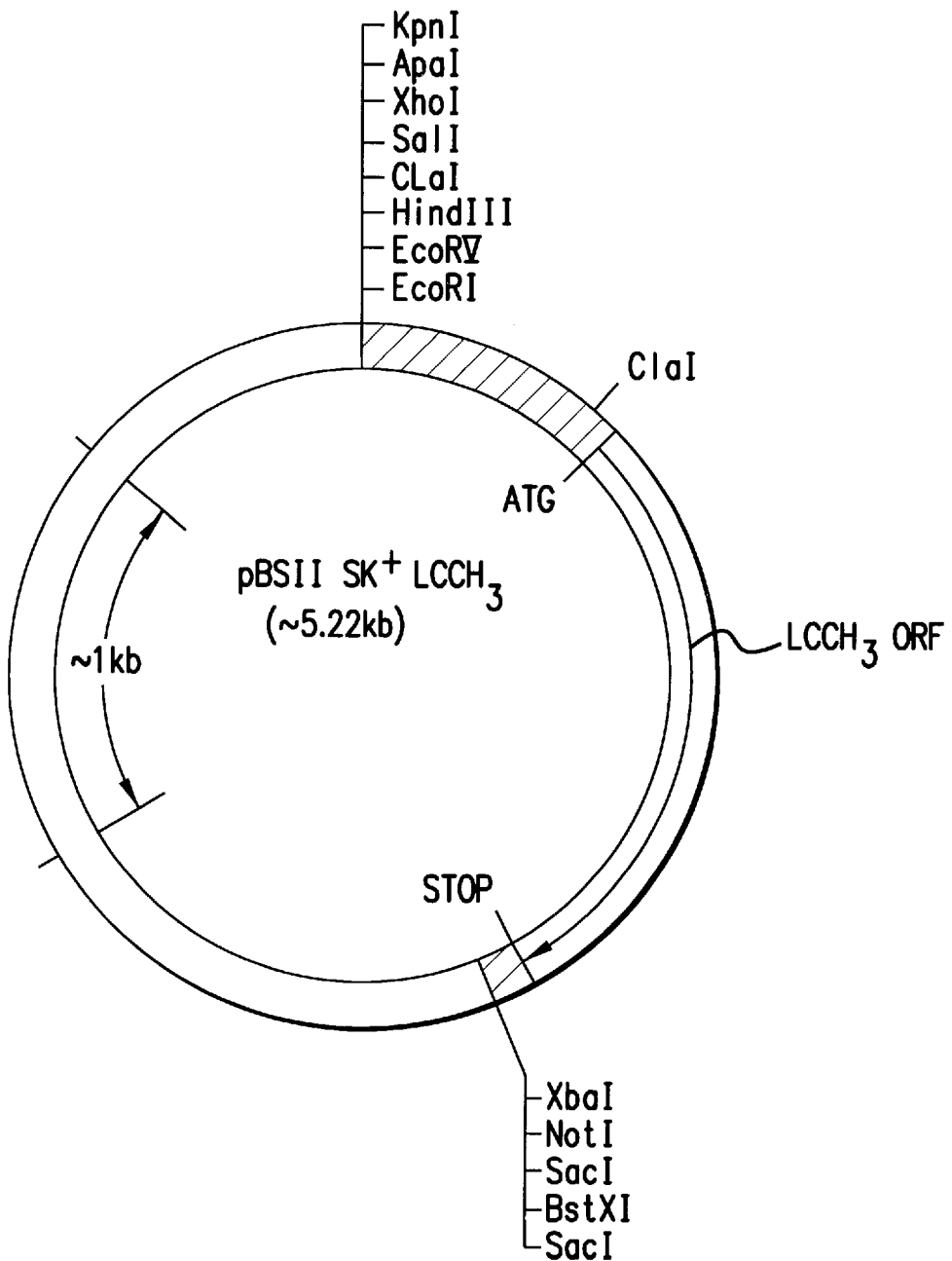
FIG. 4 depicts the plasmid pBSIISK$^+$-LCCH3.
Figure 5:
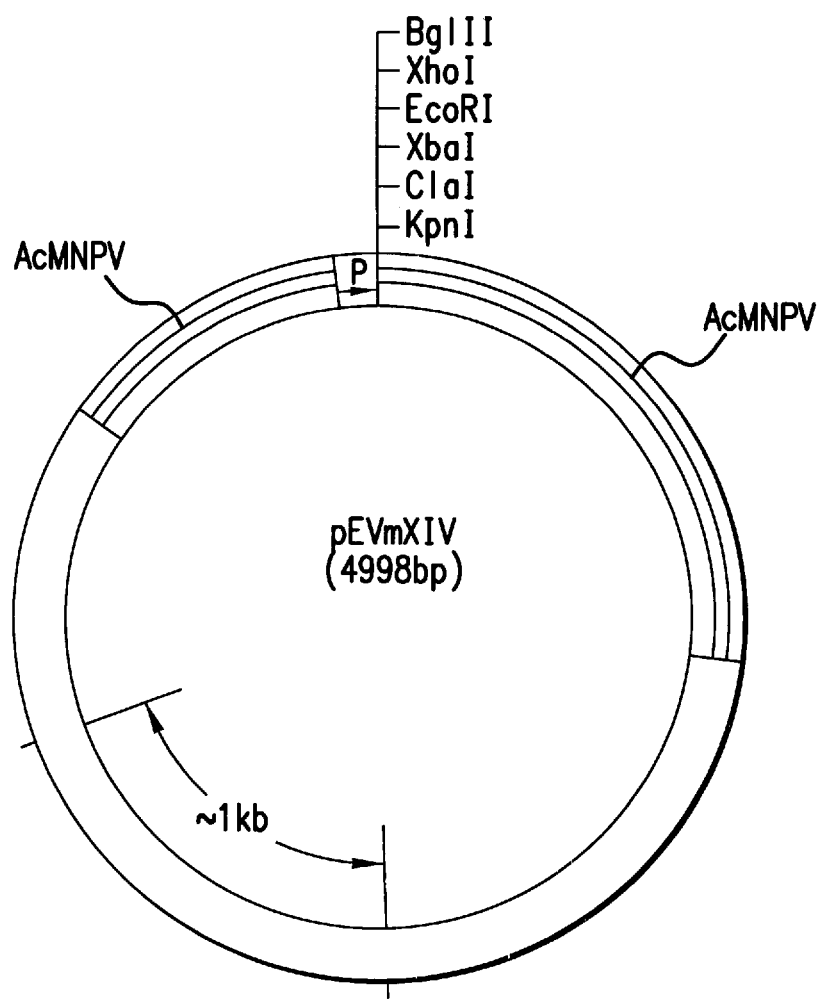
FIG. 5 depicts the plasmid pEVmXIV.
Figure 6:
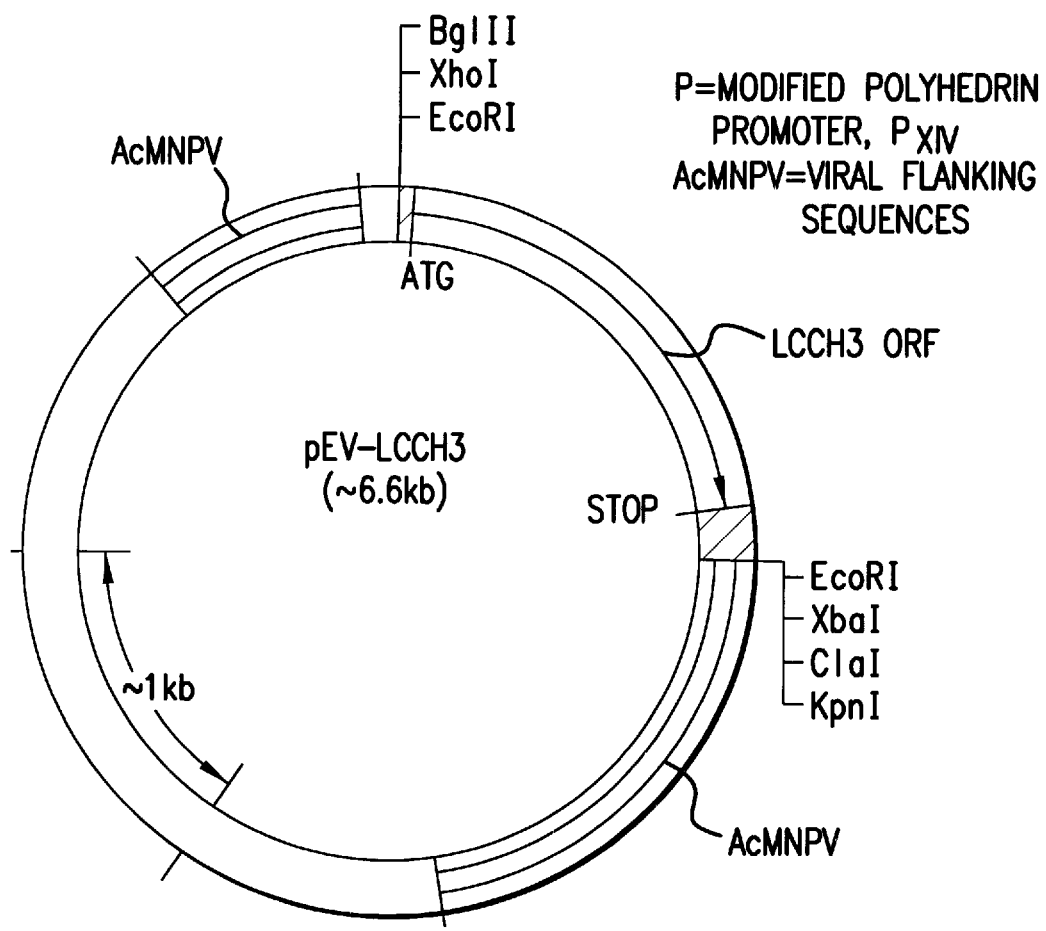
FIG. 6 depicts the plasmid pEV-LCCH3.
Figure 7:
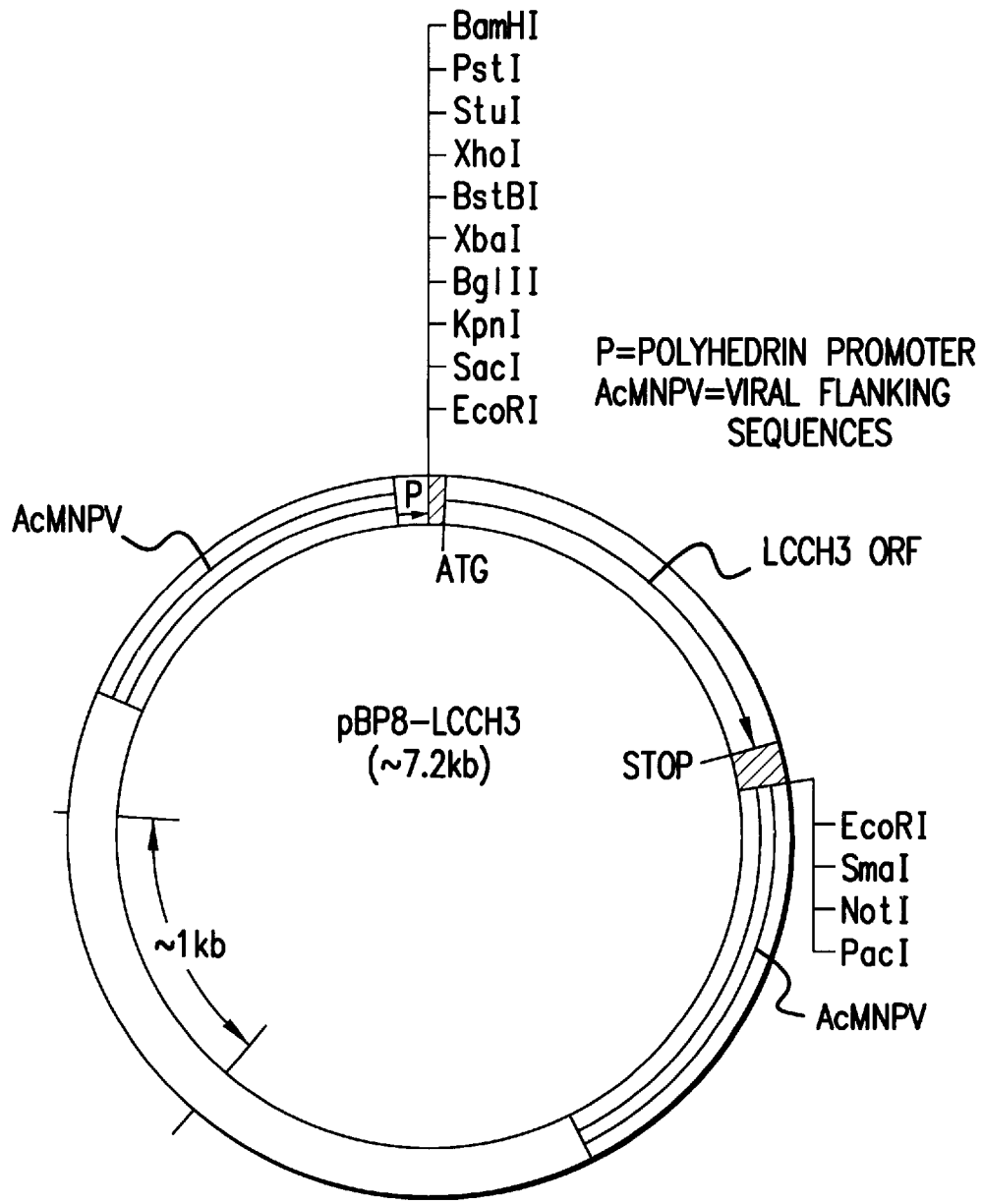
FIG. 7 depicts the plasmid pBP8-LCCH3.

The plasmid pBP8-LCCH3 was constructed as follows. A 1.65 kb ClaI/XbaI DNA fragment, containing the complete coding sequence of LCCH3, was excised from the plasmid, pBSIISK⁺-LCCH3 obtained from Dr. David Sonderlund, Department of Entomology, New York State Agricultural Experiment Station, Geneva, N.Y. (FIG. 4), blunt-ended, and then cloned into the blunt-ended EcoRI site of the baculovirus transfer vector, pEVmXIV (FIG. 5) (Ooi et al. (1989) *J. Mol. Biol.* 210:721 to provide pEV-LCCH3 (FIG. 6). This plasmid contains LCCH3 under the control of a modified polyhedrin promoter and flanked on either side by 760 bp and 1,500 bp of viral sequence respectively. Subsequently, LCCH3 was removed from pEV-LCCH3 with EcoRI and this fragment cloned into the EcoRI site of pBacPAK8 to produce the 7.2 kb plasmid, pBP8-LCCH3 (FIG. 7) which contains LCCH3 under the control of the wild-type polyhedrin promoter and flanked on either side by 1,250 bp and 1,433 bp of viral sequence, respectively. Restriction enzyme mapping was used to confirm the correct insertion of the LCCH3 cDNA in pEV-LCCH3 and pBP8-LCCH3.

The baculovirus transfer vector pBP8-Rdl was constructed as follows. The plasmid, pNB14.1 (ffrench-Constant et al., (1991) *Proc. Natl. Acad. Sci. USA* 88:7209), containing a cDNA (designated as 14.1), which encodes full-length Rdl, was provided by R. ffrench-Constant (University of Wisconsin, Madison, Wis.). To both facilitate the excision of Rdl from pNB14.1 and to eliminate undesirable 5' upstream untranslated leader sequences, which potentially could reduce protein expression levels, an XhoI restriction endonuclease site was inserted into the 5' upstream leader sequence of pNB14.1 by PCR. Using primers Pr14.1SA-18 (5'-AAAACTCGAGGCACCACCATGAG-3'; SEQ ID NO:5) and Pr14.1NA+131 (5'GCACTGTATGGATCCGTTTGTGG-3'; SEQ ID NO:6) and pNB-14.1 as the template, a 149 base pair (bp) DNA fragment (designated as 14.1mA(N-frag) which spanned from nucleotide (nt) −18 to nt +131 of pNB14.1, was synthesized. The 14.1mA(N-frag) fragment was gel purified, digested with both XhoI and BamHI, and then cloned in XhoI and BamHI-digested pBlueScript KS⁻ (pBSM-KS) to give pBSM-14.1mA(N-frag). pBSM-14.1mA(N-frag) consists of a deletion of 80 bp from nt −95 (the HindIII site at nt 2423 within the pNB40 vector sequence) to nt −15, and the incorporation of an XhoI site at nt −14 of pNB14.1. Sequencing of this fragment also revealed a PCR-induced mutation in which the T at position +9 was changed to a C. Fortuitously, this change resulted in a 'silent' mutation in that both the original codon, GAT, and the mutated codon, GAC, code for aspartate. The cloning intermediate, pBSM-14.1 mA, which contained a full-length cDNA encoding Rdl, was constructed by excising the remaining 1,848 bp C-terminal portion of Rdl from pNB-14.1 using BamHI and NotI. This fragment was gel-purified and then cloned into pBSM-14.1 mA(N-frag) which also had been digested previously with the same restriction enzymes.

The baculovirus transfer vectors, pEV-14.1 mA (hereafter designated as pEV-Rdl) and pBP8-14.1 mA (hereafter designated as pBP8-Rdl), were constructed as follows: pEV-Rdl was constructed by first digesting pBSM-14.1 mA with NotI and then blunting the ends by fill-in with T4 DNA polymerase and dNTPs. Final digestion with XhoI excised the full-length cDNA encoding Rdl. The Rdl containing fragment was gel-purified and then cloned into pEVmXIV which was prepared by digestion with KpnI, blunting the ends by T4 DNA polymerase nuclease activity, and then digestion with XhoI. pBP8-DmRdl was constructed by first digesting pEV-14.1 mA with BsmI, blunting the ends by fill-in with T4 DNA polymerase and dNTPs, and then digesting with BglII. The Rdl-containing fragment was gel-purified and then cloned into pBP8 which was prepared by digestion with SmaI and BglII.

Spodoptera frugiperda (Sf9) cells obtained from the American Tape Culture Collection (ATCC), 12301 Parklawn Drive, Rockville, Md. 20852-1776 were co-transfected either with pBP8-Grd, pBP8-LCCH3, or pBP8-Rdl and Bsu36I digested vBacPAK6 viral DNA (CLONTECH Laboratories, Inc.) using a lipofectin procedure. Bsu36I-digestion of vBacPAC6 excises an essential gene, thereby inhibiting the large viral DNA fragment from replicating and producing viable virus. Recombination of pBP8-Grd or pBP8-LCCH3 with the Bsu36I-digested viral DNA rescues the essential gene and restores the viability of the virus. The parental BacPAC6 virus also contains a copy of the lacZ gene under the control of the polyhedrin promoter which is substituted by the cDNA during the allelic replacement reaction. Therefore, recombinant virus produce white plaques in cell monolayers in the presence of X-GAL. Restriction enzyme mapping was used to confirm the correct insertion of the Grd, LCCH3, or Rdl cDNAs in the virus. The recombinant viruses containing either the Grd, LCCH3, or Rdl gene are referred to as vBP8-Grd, vBP8-LCCH3, or vBP8-Rdl, respectively.

Figure 8:
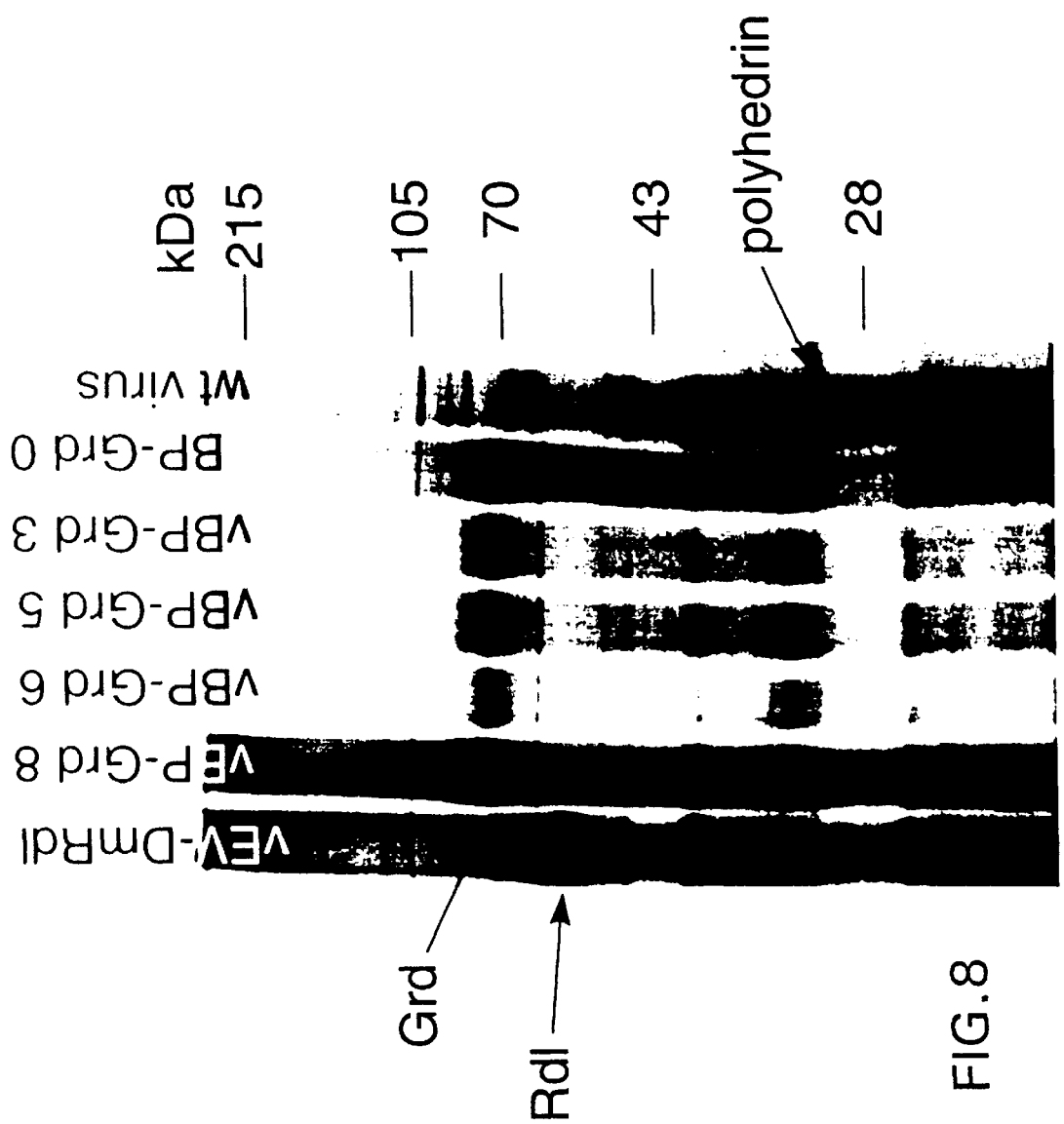
FIG. 8 depicts the expression of Grd in vBP8-Grd-infected insect cells.
Figure 9:
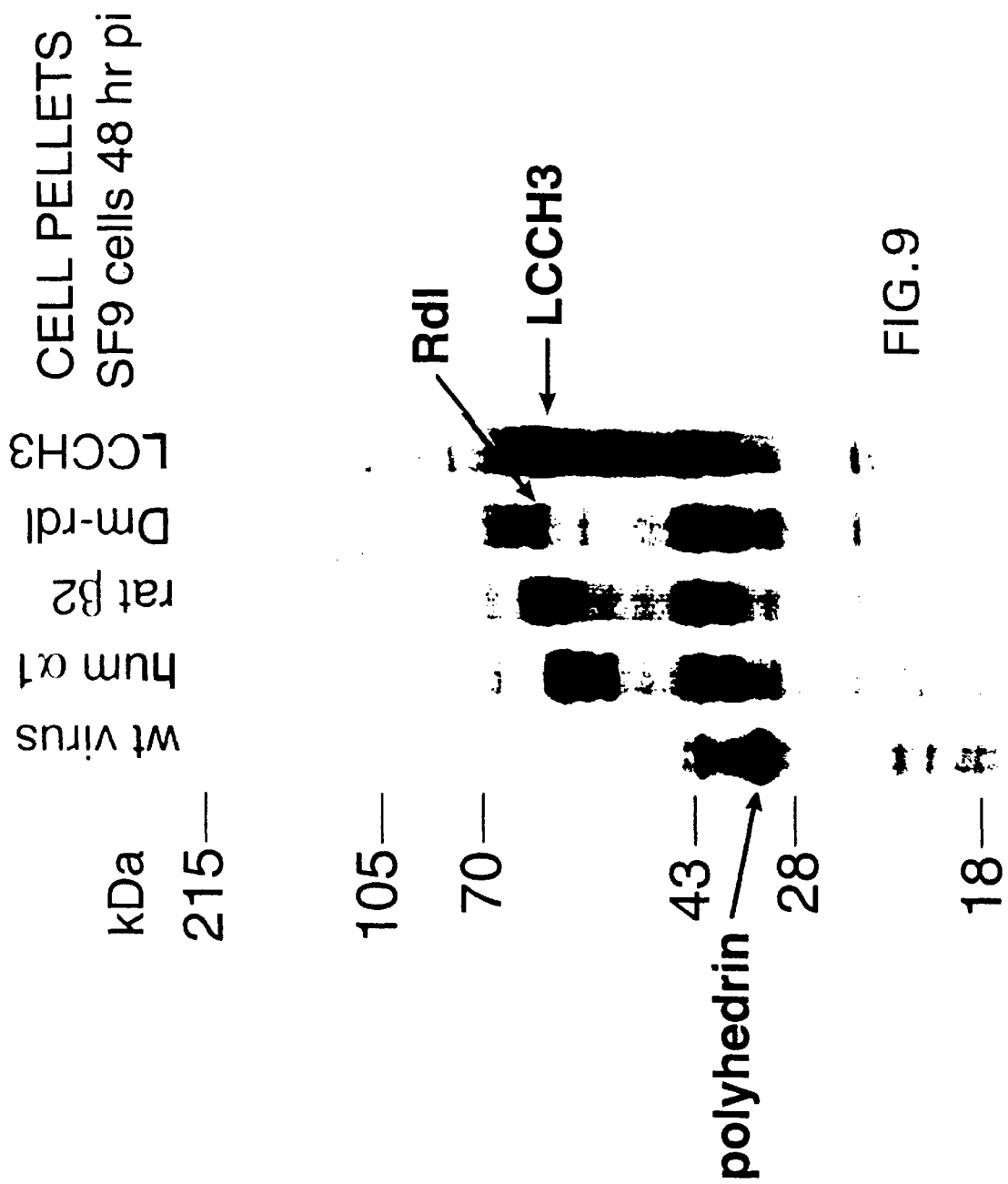
FIG. 9 depicts the expression of LCCH3 in vBP8-LCCH3-infected insect cells.

Expression of the Grd, LCCH3, or Rdl subunits in vBP8-Grd-, vBP8-LCCH3-, or vBP8-Rdl-infected insect cells was analyzed by SDS polyacrylamide gel electrophoresis (SDS-PAGE) of infected cell extracts. The expression of viral genes follows a predictable temporal course after cells are infected at a relatively high multiplicity of infection (moi) of 5 or more plaque forming units (pfu) per cell. Genes, under the control of the polyhedrin promoter, are transcribed beginning at around 18 hours post-infection and can continue up to around 96 hours post-infection. Infected cells were pulse-labeled with [$^{35}$S]methionine/[$^{35}$S]cysteine at 48 hours post-infection. Whole cell lysates were fractionated into soluble and insoluble protein components by centrifugation and then analyzed by SDS-PAGE. The proteins were visualized first by staining with Coomassie blue, and then by fluorography and exposure to film. Examples of Grd, LCCH3, and Rdl protein expression in insect cells at 48 hours post-infection is shown in FIGS. 8 and 9. The viruses that were used to infect the cells from which the insoluble protein components were derived are indicated at the top of each lane.

FIG. 8 demonstrates that the Grd gene is expressed in vBP8-Grd-infected insect cells to provide an infected-insect cell-specific protein having a relative molecular weight ($M_r$) of 69 kilodaltons (kDa). FIG. 9 demonstrates that the LCCH3 gene is expressed in vBP8-LCCH3-infected insect cells to provide an infected-insect cell-specific protein having an $M_r$ of 57 kDa.

FIGS. 8 and 9 demonstrate that the Rdl gene is expressed in vBP8-Rdl-infected cells to provide a protein having an expected $M_r$ of 60 kDa.

Insect cells infected with either vBP8-Grd, vBP8-LCCH3, or co-infected with vBP8-Grd and vBP8-LCCH3 were analyzed for the expression and assembly of functional GABA-gated chloride channels. Whole cell voltage clamp recordings were made at between 30 and 36 hours post-infection. Depolarization was not detected in any of the three infected cells types with GABA applications of up to 1 mM. Insect cells infected with either vBP8-Grd, vBP8-LCCH3, or co-infected with vBP8-Grd and vBP8-LCCH3 were also analyzed for the assembly of GABA recognition sites using [$^3$H]muscimol and for channel binding sites using [$^3$H]4-n-propyl-4'-ethynylbicycloorthobenzoate ([$^3$H]EBOB; Deng et al. (1993) Pest. Biochem. Physiol. 47:98). High levels of specific binding of [$^3$H]muscimol were detected in cells 3 days after co-infection with vBP8-Grd and vBP8-LCCH3. However, no specific [$^3$H]EBOB binding was detected in cells infected with any combination of virus. These results indicate that a GABA-recognition site is formed by co-expression of cDNA encoding Grd and LCCH3.

EXAMPLE 2

[$^3$H] Muscimol Radioligand Binding Assay

High Five™ cells (derived from the cabbage loper, Trichoplusia ni, Invitrogen Corp.) were infected with vBP8-Rdl, vBP8-LCCH3, or vBP8-Grd, either singly or in various combinations. Cells were harvested at 3 days post-infection in tubes of approximately 6×10$^7$ cells per tube, the cells were pelleted by centrifugation, the supernatants discarded, and the pellets immediately stored at −80° C. This amount of tissue is sufficient for one 96-well microtiter plate. Membranes were prepared by first thawing and then resuspending the cell pellet in 25 mL of 10 mM phosphate buffer pH 7.4. The cells were gently homogenized with five strokes in a glass/Teflon homogenizer and the membranes pelleted by centrifugation at 120,000 g for 30 minutes. The membrane pellet was resuspended in 25 mL of 10 mM phosphate buffer pH 7.4, re-pelleted as above, and the pellet finally resuspended in 3 mL of buffer. The protein concentration was determined by the Bradford method (Bradford (1976) Anal. Biochem. 79:248) and then adjusted to 625 µg of protein per mL of 10 mM PBS, pH 7.4.

The radioligand binding assays were composed of 200 µL membrane preparation (containing 125 µg protein), 100 µL of [$^3$H] muscimol (to give a final concentration of 5 nM), 20 µL of unlabeled test compound, buffer or unlabeled muscimol, and 680 µL of 10 mM PBS, pH 7.4. Non-specific binding was defined as that remaining in the presence of 10 µM GABA. The reactions were incubated for 90 minutes at 4° C., and then terminated by filtration through Whatman GF/B glass fiber filters. Filters were washed with two 5 mL aliquots of cold buffer, and the radioactivity remaining on the filters was determined by liquid scintillation. Multiple assays were performed to test numerous compounds.

The co-expression of human α1 and rat β2 receptor subunit proteins in insect cells via baculovirus vectors was used as a positive control in binding and functional assays. The co-expression of an α and β subunit is known to result in the formation of GABA-responsive receptors that bind muscimol and EBOB at high specific levels. The cDNAs encoding the human α1 and rat β2 subunits were obtained from Richard ffrench-Constant at the University of Wisconsin, Madison, Wis. and used to make the baculovirus expression vectors (viruses) vEV-humα1 and vEV-ratβ2 via pEV$_{MXIV}$ intermediates.

The percentage specific binding, equilibrium ($K_d$), maximum number of binding sites ($B_{max}$), and inhibition constants for test compounds ($IC_{50}$) for [$^3$H] muscimol binding to the various GABA receptor subunits were determined by kinetic and equilibrium analysis of saturation binding data (Limbird, 1986) supra.

Table I presents the specific binding values for [$^3$H] muscimol binding in membranes of High Five™ cells infected with vBP8-Rdl, vBP8-LCCH3, vBP8-Grd, vBP8-Grd/vBP8-LCCH3, or vBP8-Grd/vBP8-LCCH3/vBP8-Rdl.

TABLE 1

| Subunit Proteins | % Specific Binding |
| --- | --- |
| Drosophila Rdl | 55 |
| Drosophila Grd | 10 |
| Drosophila LCCH3 | 10 |
| Drosophila Grd and LCCH3 | 85 |
| Drosophila Rdl, Grd and LCCH3 | 60 |
| Human α1 and rat β2 | 80 |

Table 2 presents the $K_d$ and $B_{max}$ values for [$^3$H] muscimol binding. Data for housefly heads are from Lunt et al. (1985) *Neurochem. Int.* 7:751. Data for rat brain were obtained from previous assays performed by the present inventors using standard methods.

TABLE 2

| Subunit Proteins | Kd (nM) | Bmax[1] |
| --- | --- | --- |
| Drosophila Rdl | 12 | 0.11 |
| Drosophila Grd | >10,000 | — |
| Drosophila LCCH3 | >10,000 | — |
| Drosophila Grd and LCCH3 | 12 | 1.85 |
| Drosophila Rdl, Grd and LCCH3 | 38 | 0.64 |
| Housefly heads | 40 | 0.02 |
| Rat brain | 28 | 1.50 |

[1]pmol [3H] muscimol bound per mg of protein

The data in Tables 1 and 2 demonstrate that cells that are co-infected with vBP8-Grd and vBP8-LCCH3 have the highest levels of specific [$^3$H]-muscimol binding (Table 1) and the same $K_d$ as that of vBP8-Rdl-infected cells but a 15-fold higher maximum number of binding sites ($B_{max}$, Table 2).

Table 3 presents $IC_{50}$ values for the tested compounds which include known $GABA_A$ agonists and antagonists, $GABA_B$ agonists and antagonists, and a $GABA_C$ agonist. The $IC_{50}$ is the molar concentration of the test compound required to produce half-maximal displacement of [$^3$H] muscimol from the GABA-binding site of the GABA receptor subunits. Data from fly heads and rat brains were obtained as described in Table 2.

TABLE 3

|  | Rdl | Grd/LCCH3 | Grd/LCCH3/Rdl IC$_{50}$ (nM) | Fly Heads | Rat Brain |
| --- | --- | --- | --- | --- | --- |
| GABA$_A$ Agonists: | | | | | |
| Muscimol | 12 | 15 | 23 | 30 | 43 |
| GABA | 37 | 38 | 32 | 40 | 255 |
| Isoguavacine | 260 | 190 | — | 100 | 289 |
| Isonipecotic acid | 1,705 | 2,678 | — | — | 1,425 |
| Piperidine-4-sulfonate | i.a.[1] | i.a. | — | — | 297 |
| Antagonists: | | | | | |
| Bicuculline | i.a. | i.a. | — | — | 19,000 |
| β-Hydrastine | i.a. | i.a. | — | — | 2,610 |
| Gabazine | i.a. | i.a. | — | — | 483 |
| GABA$_B$ Agonists: | | | | | |
| Baclofen | i.a. | i.a. | — | not tested | i.a. |

TABLE 3-continued

|  | Rdl | Grd/LCCH3 | Grd/LCCH3/Rdl IC$_{50}$ (nM) | Fly Heads | Rat Brain |
| --- | --- | --- | --- | --- | --- |
| SKF-97541 | i.a. | i.a. | — | not tested | i.a. |
| Antagonists: | | | | | |
| 5-amino-valeric acid | 2,104 | 749 | — | not tested | i.a. |
| GABA$_C$ Agonists: | | | | | |
| cis-4-amino-crotonic acid | 2,915 | 1,618 | — | not tested | i.a. |

[1]i.a. = IC$_{50}$ > 10$^{-3}$M

The data in Table 3 demonstrate that cells which are co-infected with vBP8-Grd and vBP8-LCCH3 exhibit a pharmacology similar to that of vBP8-Rdl-infected cells and native insect tissue.

EXAMPLE 3

Production of a Permanently Transformed Insect Cell Line Expressing Both Grd and LCCH3 Subunit Proteins The vector pMK33/pMtHy (FIG. 10) (Krasnow et al. (1989) *Cell* 57:1031; Kaufman et al. (1989) *Cell* 59:359) is an 8.5 kb plasmid which was obtained from Dr. David Hogness, Department of Biochemistry and Developmental Biology, Stanford University Medical Center, Stanford, Calif. It contains the *Drosophila metallothionein* (Mt) promoter preceded by a multiple cloning site for the insertion of heterologous genes, and a hygromycin resistance gene under the control of the copia LTR promoter which allows selection of stably transformed cell lines carrying the plasmid.

Figure 12:
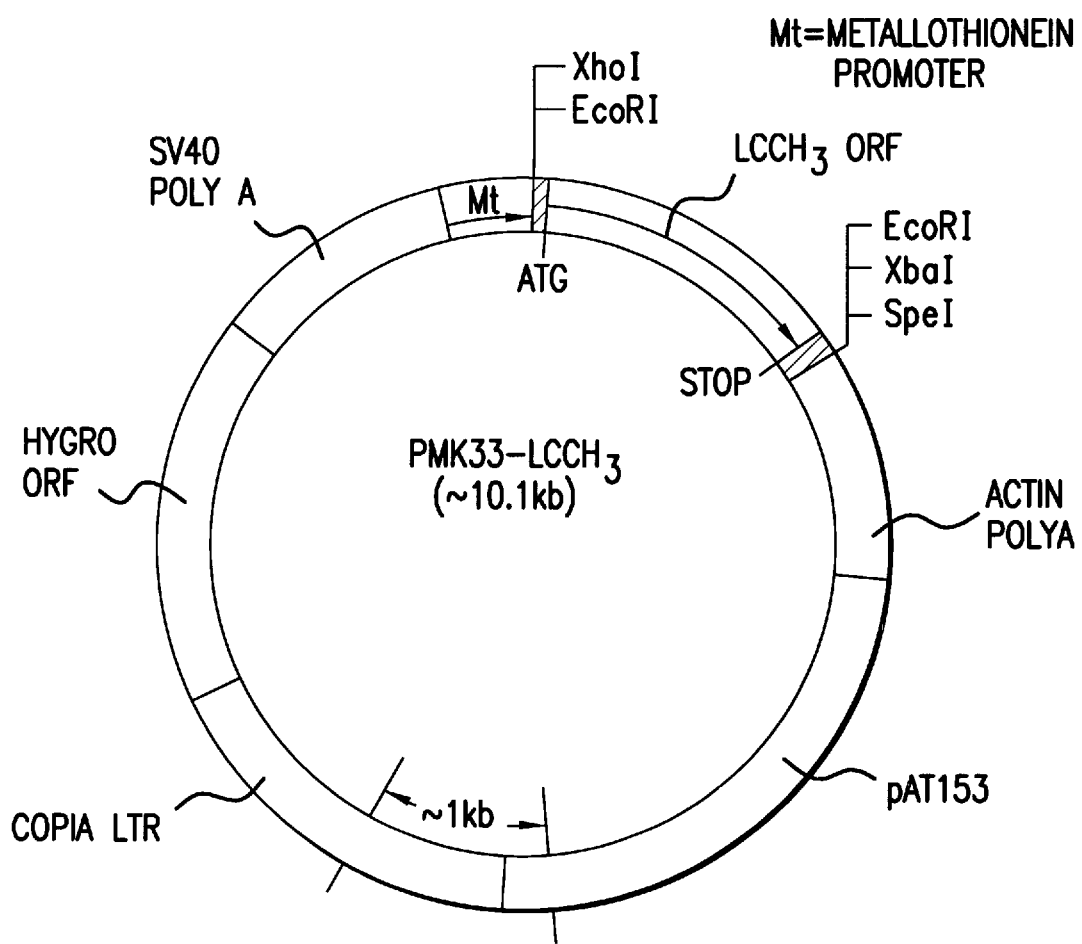
FIG. 12 depicts the plasmid pMK33-LCCH3.

A 1.6 kb XhoI/BglII DNA fragment, containing the complete coding sequence of LCCH3, was excised from the plasmid, pBP8-LCCH3. This fragment was cloned into the XhoI/BamHI site of pMK33/pMtHy, to produce the 10.1 kb plasmid, pMK33-LCCH3, which contains LCCH3 under the control of the metallothionein (Mt) promoter. Restriction enzyme mapping was used to confirm the correct insertion of the LCCH3 cDNA in pMK33-LCCH3 (FIG. 12).

Figure 11:
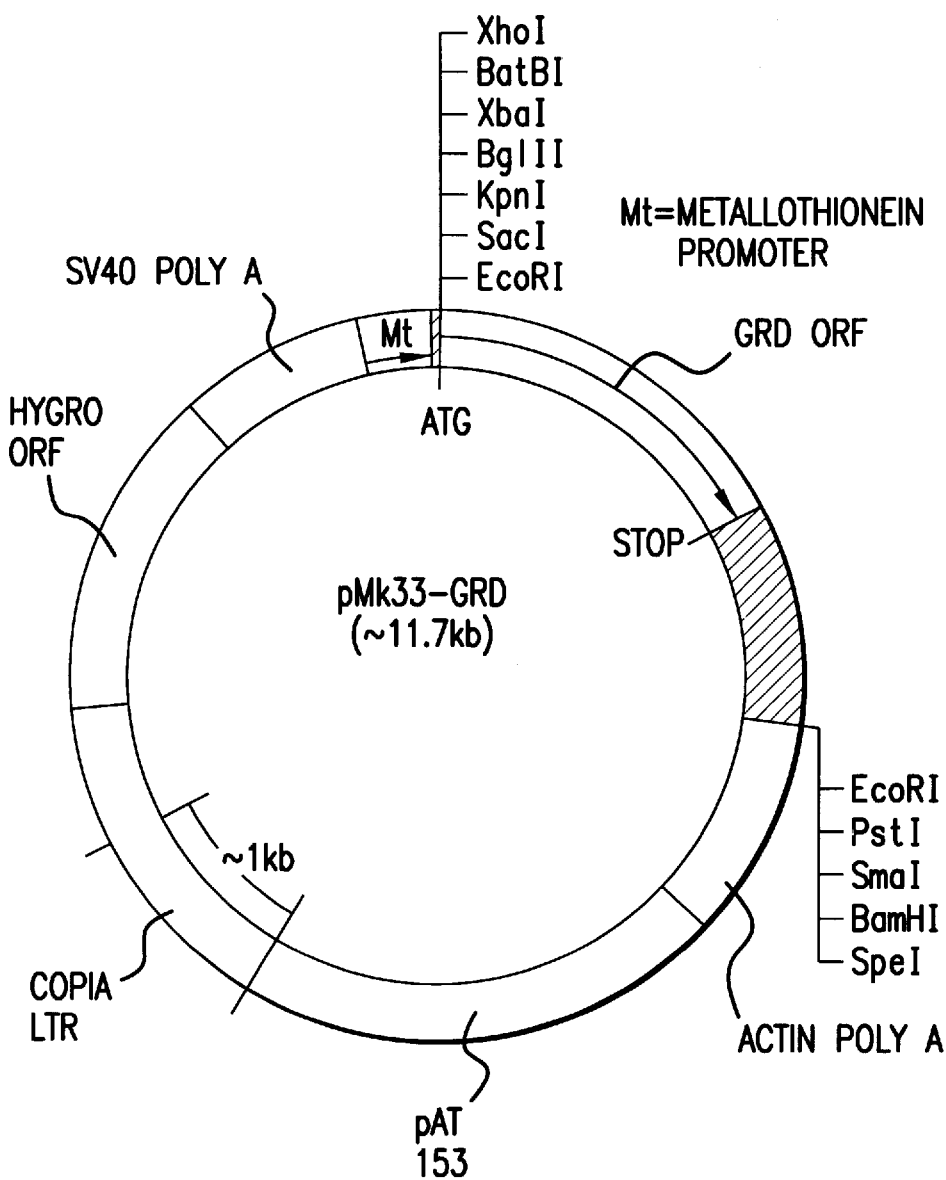
FIG. 11 depicts the plasmid pMK33-Grd.

A 3.2 kb XhoI/blunt-ended NotI DNA fragment, containing the complete coding sequence of Grd, was excised from the plasmid, pBP8-Grd described in Example 1. This fragment is cloned into the XhoI/EcoRV site of pMK33/pMtHy. The resulting 11.7 kb plasmid, designed as pMK33-Grd (FIG. 11), contains Grd under the control of the metallothionein promoter. Restriction enzyme mapping is used to confirm the correct insertion of the Grd cDNA in pMK33-Grd.

Drosophila Schneider Line 1 cells (SL1) obtained from Dr. Roland Rueckert, Institute for Molecular Virology, University of Wisconsin, Madison, Wis. are co-transfected with pMK33-Grd and pMK33-LCCH3 using the lipofectin procedure described in O'Reilly et al., *Baculovirus Expression Vectors: A Laboratory Manual*, W. H. Freeman & Co., New York 1992. Insect cell transformants are selected for with tissue culture media supplemented with 200 μg Hygromycin B per mL. In the ensuing two to three week period, clonal colonies are isolated and amplified to large stocks of about 100 mL of 2 to 5×10$^6$ cells per mL. The expression of Grd and LCCH3 proteins is induced by adding cadmium chloride to the growth medium to achieve a final concentration of 10 μM Cd⁺⁺. Forty-eight hours after induction, cells are homogenized in PBS and the membranes isolated by centrifugation. The membranes are then used for binding analysis with [$^3$H]muscimol as described in Example 2.

We claim:

1. A host cell comprising a first expression vector comprising a first nucleic acid encoding the insect receptor GABA subunit LCCH3 having the amino acid sequence of SEQ. NO: 2, wherein said first nucleic acid is operably linked to a first promoter, and a second expression vector comprising a second nucleic acid encoding the insect GABA receptor Grd having the amino acid sequence SEQ. ID NO: 4, wherein said second nucleic acid is operably linked to a second promoter.

2. A host cell comprising an expression vector wherein said expression vector comprises a first nucleic acid encoding the insect receptor GABA subunit LCCH3 having the amino acid sequence of SEQ. ID NO: 2, and a second nucleic acid encoding the insect GABA receptor Grd having the amino acid sequence of SEQ. ID NO: 4, wherein said first and second nucleic acids are operably linked to one or more regulatory elements.

3. The host cell of claim 1 or 2, wherein said cell is a bacterial, yeast, insect or mammalian cell.

4. The host cell of claim 1 or 2, wherein said cell is an insect cell.

5. The host cell of claim 4, wherein said insect cell is a *Spodoptera frugiperda, Trichoplusia ni* or Drosophila Schneider Line 1 cell.

6. The host cell of claim 1 or 2, wherein said nucleic acid encoding the insect GABA receptor subunit LCCH3 has the nucleotide sequence of SEQ ID NO:1.

7. The host cell of claim 1 or 2, wherein said nucleic acid encoding the insect GABA receptor subunit Grd has the nucleotide sequence of SEQ ID NO:3.

8. The host cell of claim 1, wherein said first expression vector and said second expression vector are baculovirus expression vectors.

9. The host cell of claim 1, wherein said first promoter and said second promoter are independently selected from the group consisting of a metallothionein promoter, heat shock promoter, dexamethasone promoter, alcohol dehydrogenase promoter, baculovirus early promoter, baculovirus late promoter, baculovirus very late promoter, and baculovirus hybrid promoter.

10. A composition comprising cell membranes containing the insect GABA receptor subunits LCCH3 and Grd and a physiological buffer, wherein said cell membranes are obtained from the host cell of claim 1 or 2, and wherein said first and second nucleic acids are expressed by said host cell.

11. A kit for measuring the ability of a compound to bind to the GABA recognition site of an insect GABA receptor, wherein said kit contains a container containing cell membranes comprising the insect GABA receptor subunits LCCH3 and Grd, wherein said cell membranes are obtained from the host cell of claim 1 or 2, and wherein said first and second nucleic acids are expressed by said host cell.

12. The host cell of claim 2, wherein said expression vector is a baculovirus expression vector.

13. An insect host cell comprising a first heterologous nucleic acid encoding the insect GABA receptor LCCH3 having the amino acid sequence of SEQ. ID NO:2, and a second heterologous nucleic acid encoding the insect GABA receptor Grd having the amino acid sequence of SEQ. ID NO: 4, wherein said insect host cell is a *Spodoptera frugiperda, Trichoplusia ni* or Drosophila Schneider Line 1 cell.

14. The insert host cell of claim 13 wherein said first nucleic acid encoding the insect GABA receptor subunit LCCH3 has the nucleotide sequence of SEQ ID NO:1.

15. The insert host cell of claim 13 wherein said second nucleic acid encoding the insect GABA receptor subunit Grd has the nucleotide sequence of SEQ ID NO:3.

16. A permanently transformed insect cell line comprising a first nucleic acid encoding the insect GABA receptor subunit LCCH3 having the amino acid sequence of SEQ. ID NO: 2, wherein said first nucleic acid is operably linked to a first promoter, and a second nucleic acid encoding the insect GABA receptor subunit Grd having the amino acid sequence of SEQ. NO: 4, wherein said second nucleic acid is operably linked to a promoter.

17. A baculovirus expression vector comprising a first nucleic acid having a nucleotide sequence encoding the amino acid sequence of SEQ. ID NO: 2; and a second nucleic acid having a nucleotide sequence encoding the amino acid sequence of SEQ. ID NO: 4.

18. A kit for measuring the ability of a compound to bind to the GABA recognition site of an insect GABA receptor, wherein said kit contains a container containing a host cell comprising a first expression vector comprising a first nucleic acid encoding the insect receptor GABA subunit LCCH3 having the amino acid sequence of SEQ. ID NO: 2, wherein said first nucleic acid is operably linked to a first promoter, and a second expression vector comprising a second nucleic acid encoding the insect GABA receptor Grd having the amino acid sequence of SEQ. ID NO: 4, wherein said second nucleic acid is operably linked to a second promoter, and wherein said host cell expresses or is capable of expressing the nucleic acid encoding the insect GABA receptor LCCH3 and the nucleic acid encoding the insect GABA receptor subunit Grd.

19. A kit for measuring the ability of a compound to bind to the GABA recognition site of an insect GABA receptor, wherein said kit contains a first container containing a host cell comprising an expression vector, wherein said expression vector comprises a first nucleic acid encoding the insect receptor GABA subunit LCCH3 having the amino acid sequence of SEQ. ID NO: 2, and a second nucleic acid encoding the insect GABA receptor Grd having the amino acid sequence of SEQ. ID NO:4, wherein said first and second nucleic acids are operably linked to one or more regulatory elements.

20. A method of measuring the ability of a compound to bind to the GABA recognition site of an insect GABA receptor by determining the GABA receptor-binding activity of said compound, wherein said insect GABA receptor comprises Grd and LCCH3 subunits, comprising the steps of:

incubating, in aqueous solution, a known amount of host cells or membranes obtained from said host cells, wherein said host cells comprise a first expression vector comprising a first nucleic acid encoding the insect receptor GABA subunit LCCH3 having the amino acid sequence of SEQ. ID NO: 2; wherein said first nucleic acid is operably linked to a first promoter, and a second expression vector comprising a second nucleic acid encoding the insect GABA receptor Grd having the amino acid sequence of SEQ. ID NO: 4; wherein said second nucleic acid is operably linked to a second promoter, wherein said first and second nucleic acids are coexpressed in said host cell to form a GABA receptor that binds muscimol, and [$^3$H]-muscimol in known amount that binds to said known amount of host cells or membranes, and varied known amounts of a compound to be tested for its ability to bind to said GABA recognition site for a time and under conditions suitable for a portion of said [$^3$H]-muscimol to bind to said host cells or membranes;

separating the cells or membranes from the [$^3$H]-muscimol that is not bound to the cells or membranes; and determining the GABA receptor binding activity of said compound.

21. A method of measuring the ability of a compound to bind to the GABA recognition site of an insect GABA receptor by determining the GABA receptor-binding activity of said compound, wherein said insect GABA receptor comprises Grd and LCCH3 subunits, comprising the steps of:

incubating, in aqueous solution, a known amount of host cells or membranes obtained therefrom, wherein said host cells comprise an expression vector comprising a first nucleic acid encoding the insect receptor GABA subunit LCCH3 having the amino acid sequence of SEQ. ID NO: 2; and a second nucleic acid encoding the insect GABA receptor Grd having the amino acid sequence of SEQ. ID NO: 4; wherein said first and second nucleic acids are operably linked to one or more regulatory elements, wherein said first and second nucleic acids are coexpressed in said host cell to form a GABA receptor that binds muscimol, and [$^3$H]-muscimol in a known amount that binds to said known amount of host cells or membranes, and varied known amounts of a compound to be tested for its ability to bind to said GABA recognition site for a time and under conditions suitable for a portion of said [$^3$H]-muscimol to bind to said host cells or membranes;

separating the cells or membranes from the [$^3$H]-muscimol that is not bound to the cells or membranes; and determining the GABA receptor binding activity of said compound.

22. The method of claim 20 or 21 wherein said host cells or membranes are insect host cells or insect cell membranes.

23. The method of claim 20 or 21 wherein said nucleic acid encoding the LCCH3 subunit has the nucleotide sequence of SEQ ID NO:1.

24. The method of claim 20 or 21 wherein said nucleic acid encoding the Grd subunit has the nucleotide sequence of SEQ ID NO:3.

25. The method of claim 20 or 21 wherein separation of cells or membranes from unbound [$^3$H]-muscimol is by filtration.

26. The method of claim 20 or 21 wherein the GABA receptor binding activity of said compound is determined by calculating the IC$_{50}$ value for said compound.

* * * * *

UNITED STATES PATENT AND TRADEMARK OFFICE
CERTIFICATE OF CORRECTION

PATENT NO. : 5,854,002

DATED : December 29, 1998

INVENTOR(S) : Tomalski et al.

It is certified that error appears in the above-identified patent and that said Letters Patent is hereby corrected as shown below:

Col. 28, line 39, "insert" should read --insect--.

Col. 28, line 42, "insert" should read --insect--.

Signed and Sealed this

First Day of February, 2000

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1491 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
ATGACATGTT TTACGCGCGT CGGAGTATCC TGTAGCCTGT TCTTTTTCCT ACTGGGCGCC      60
CAGCTACAAT TGATTCGATG CATTCGAAAG GATGTACTAG CTGGCCGCCT TGAGAACGTN     120
ACGCAAACAA TATCAAACAT ACTGCAAGGA TACGATATTC GACTTAGGCC CAATTTCGGA     180
GGAGAGCCAC TACATGTCGG CATGGATTTG ACCATCGCCA GCTTTGATGC CATATCAGAA     240
GTTAACATGG ATTATACGAT AACAATGTAT TTAAATCAGT ATTGGCGCGA CGAGCGTTTG     300
GCATTTAATA TCTTTGGACA ATATTTCGAC GATGAGAATG ATGATGGCAT AAGCGATGTG     360
CTGACATTAT CCGGAGACTT TGCTGAAAAG ATATGGGTAC CGGATACGTT CTTCGCCAAT     420
GACAAAAACA GTTTTCTGCA CGATGTCACC GAAAGGAACA AACTGGTGCG ACTTGGCGGC     480
GATGGAGCTG TTACTTATGG CATGAGATTC ACCACGACCC TCGCCTGCAT GATGGATCTG     540
CACTACTATC CATTGGACTC GCAGAATTGC ACTGTGGAAA TTGAGAGCTA TGGATACACG     600
GTCAGCGATG TGGTCATGTA CTGGAAGCCA ACGCCAGTGC GCGGAGTGGA GGATGCGGAG     660
CTGCCGCAGT TCACCATCAT TGGGTATGAG ACCAATGACC GAAAGGAGCG GCTGGCCACT     720
GGAGTCTATC AGCGCCTCTC GCTCTCATTC AAACTGCAAC GGAATATCGG ATACTTTGTA     780
TTCCAAACTT ATCTGCCCAG CATTCTGATC GTAATGCTGT CGTGGGTCTC GTTCTGGATT     840
AACCACGAGG CGACGAGTGC CCGGGTTGCA TTGGGCATCA CCACGGTGCT CACCATGACC     900
ACCATTAGCA CGGGTGTTCG CAGCTCACTG CCGCGCATAT CGTATGTGAA GGCGATCGAC     960
ATTTATCTGG TCATGTGCTT CGTTTTCGTG TTCGCAGCCC TCTTGGAATA CGCTGCCGTT    1020
AACTATACTT ACTGGGGCAA AAGGGCTAAA AAGAAAATAA AGAAAGTCAA AGAATGTTGT    1080
CCAGGCAAGA TCGGAAAGAG TGAAAGATCC GAGACGTGTT CAACGACAGA GGACATTATC    1140
GAGCTGCAGG ATGTTCGAAT GAGTCCTATA CCATCTTTGC GAAGAGGTAC CTACAATGCN    1200
ACCCTCGACT CCATCGGCAC CGAGACCATG AATCTAGGAA AGTTCCCCCC AAGTTTTCGA    1260
ATAACTCGTA ATTATGGCAC CGGACATAGC CAGCTTAGAC GTCGCGCCCA AAGGGGTATC    1320
TCAACCCGCC CACGCATGTT GCACGCCCTG AAGAGAGGTG CCTCTGCTAT TAAGGCAACC    1380
ATACCGAAGA TCAAAGATGT CAATATTATT GACAAATACT CCCGAATGAT ATTTCCGATC    1440
```

AGTTTTCTTG CGTTCAATCT TGGCTACTGG CTGTTTTATA TTCTGGAATG A     1491

( 2 ) INFORMATION FOR SEQ ID NO:2:

( i ) SEQUENCE CHARACTERISTICS:
        ( A ) LENGTH: 496 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

```
Met Thr Cys Phe Thr Arg Val Gly Val Ser Cys Ser Leu Phe Phe Phe
 1               5                  10                  15
Leu Leu Gly Ala Gln Leu Gln Leu Ile Arg Cys Ile Arg Lys Asp Val
             20                  25                  30
Leu Ala Gly Arg Leu Glu Asn Val Thr Gln Thr Ile Ser Asn Ile Leu
         35                  40                  45
Gln Gly Tyr Asp Ile Arg Leu Arg Pro Asn Phe Gly Gly Glu Pro Leu
     50                  55                  60
His Val Gly Met Asp Leu Thr Ile Ala Ser Phe Asp Ala Ile Ser Glu
 65                  70                  75                  80
Val Asn Met Asp Tyr Thr Ile Thr Met Tyr Leu Asn Gln Tyr Trp Arg
                 85                  90                  95
Asp Glu Arg Leu Ala Phe Asn Ile Phe Gly Gln Tyr Phe Asp Asp Glu
             100                 105                 110
Asn Asp Asp Gly Ile Ser Asp Val Leu Thr Leu Ser Gly Asp Phe Ala
         115                 120                 125
Glu Lys Ile Trp Val Pro Asp Thr Phe Phe Ala Asn Asp Lys Asn Ser
     130                 135                 140
Phe Leu His Asp Val Thr Glu Arg Asn Lys Leu Val Arg Leu Gly Gly
145                 150                 155                 160
Asp Gly Ala Val Thr Tyr Gly Met Arg Phe Thr Thr Thr Leu Ala Cys
                 165                 170                 175
Met Met Asp Leu His Tyr Tyr Pro Leu Asp Ser Gln Asn Cys Thr Val
             180                 185                 190
Glu Ile Glu Ser Tyr Gly Tyr Thr Val Ser Asp Val Val Met Tyr Trp
         195                 200                 205
Lys Pro Thr Pro Val Arg Gly Val Glu Asp Ala Glu Leu Pro Gln Phe
     210                 215                 220
Thr Ile Ile Gly Tyr Glu Thr Asn Asp Arg Lys Glu Arg Leu Ala Thr
225                 230                 235                 240
Gly Val Tyr Gln Arg Leu Ser Leu Ser Phe Lys Leu Gln Arg Asn Ile
                 245                 250                 255
Gly Tyr Phe Val Phe Gln Thr Tyr Leu Pro Ser Ile Leu Ile Val Met
             260                 265                 270
Leu Ser Trp Val Ser Phe Trp Ile Asn His Glu Ala Thr Ser Ala Arg
         275                 280                 285
Val Ala Leu Gly Ile Thr Thr Val Leu Thr Met Thr Thr Ile Ser Thr
     290                 295                 300
```

| | | | | | | | | | | | | | | | |
|---|---|---|---|---|---|---|---|---|---|---|---|---|---|---|---|
| Gly | Val | Arg | Ser | Ser | Leu | Pro | Arg | Ile | Ser | Tyr | Val | Lys | Ala | Ile | Asp |
| 305 | | | | | 310 | | | | 315 | | | | | | 320 |
| Ile | Tyr | Leu | Val | Met | Cys | Phe | Val | Phe | Val | Phe | Ala | Ala | Leu | Leu | Glu |
| | | | | 325 | | | | | 330 | | | | | 335 | |
| Tyr | Ala | Ala | Val | Asn | Tyr | Thr | Tyr | Trp | Gly | Lys | Arg | Ala | Lys | Lys | Lys |
| | | | 340 | | | | | 345 | | | | | 350 | | |
| Ile | Lys | Lys | Val | Lys | Glu | Cys | Cys | Pro | Gly | Lys | Ile | Gly | Lys | Ser | Glu |
| | | 355 | | | | | 360 | | | | | 365 | | | |
| Arg | Ser | Glu | Thr | Cys | Ser | Thr | Thr | Glu | Asp | Ile | Ile | Glu | Leu | Gln | Asp |
| | 370 | | | | | 375 | | | | | 380 | | | | |
| Val | Arg | Met | Ser | Pro | Ile | Pro | Ser | Leu | Arg | Arg | Gly | Thr | Tyr | Asn | Ala |
| 385 | | | | | 390 | | | | | 395 | | | | | 400 |
| Thr | Leu | Asp | Ser | Ile | Gly | Thr | Glu | Thr | Met | Asn | Leu | Gly | Lys | Phe | Pro |
| | | | | 405 | | | | | 410 | | | | | 415 | |
| Pro | Ser | Phe | Arg | Ile | Thr | Arg | Asn | Tyr | Gly | Thr | Gly | His | Ser | Gln | Leu |
| | | | 420 | | | | | 425 | | | | | 430 | | |
| Arg | Arg | Arg | Ala | Gln | Arg | Gly | Ile | Ser | Thr | Arg | Pro | Arg | Met | Leu | His |
| | | 435 | | | | | 440 | | | | | 445 | | | |
| Ala | Leu | Lys | Arg | Gly | Ala | Ser | Ala | Ile | Lys | Ala | Thr | Ile | Pro | Lys | Ile |
| | 450 | | | | | 455 | | | | | 460 | | | | |
| Lys | Asp | Val | Asn | Ile | Ile | Asp | Lys | Tyr | Ser | Arg | Met | Ile | Phe | Pro | Ile |
| 465 | | | | | 470 | | | | | 475 | | | | | 480 |
| Ser | Phe | Leu | Ala | Phe | Asn | Leu | Gly | Tyr | Trp | Leu | Phe | Tyr | Ile | Leu | Glu |
| | | | | 485 | | | | | 490 | | | | | 495 | |

( 2 ) INFORMATION FOR SEQ ID NO:3:

( i ) SEQUENCE CHARACTERISTICS:
        ( A ) LENGTH: 2635 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

```
GAATTCCAAA CGCTTCATGC AATTGCTCTC GACCCGAGTG CAACTTCCGG TGAATAAATG      60
AAAATAAATA CGAGCAAAGC CGAGTCAACA CACAGCTCAG GAAGAAGGCA CTGTCATCAG     120
CAGCAGCACG ACCTCCAGAA TTGGAATTTT AATGGCGATG GGATTGGGAA TGGGAATGGC     180
AATGCGAATG AAAATGAAAA TGGGACTGGG AATGGGCATG GCAACGGGAG CCAGAGGCCA     240
GTTGGAGTGA CAAAAGTTAG ACAAACGGAT GTGTAGATTA GACCGGCAAC AACAGCAGAA     300
GACTTCGACT AAACAATAGT TGCAGCCAGC GAACAAACAG CAAACAAAAC CGAACAATAT     360
GTGCACAATG CCAGCAACAA GAGATGCATC CGGCTCCGGC GATGCATCAA CTGACCTCAT     420
CGCAGCAAGG AGCCTCTCCA GCCACCAAGG ACAGCGCTCC AACTTGCGCA TATTTAAACT     480
TTTGATTAGC TGCTGCCTCT TAATGTTGTG CATTTACCCA AATGCCTGGC CCTGGTCCAT     540
CGGCCCCGGA TCGGGACCCT TCTCCGTCTC GGCCGACAGC ATCAAGGGCC GCGGCGATAC     600
TCACCGCCTG GGTGAGATGG GCACCTCCTT ATCGTCATCC CTGCCGTCCT CGTGGCTCAC     660
```

```
CCAGAGCAAT AACCATGCAA ATATATCCGA GTTACTGGAC AATCTGCTGC GCGGCTATGA    720
CAATAGCATA CGTCCGGATT TCGGTGGACC TCCAGCCACT ATTGAAGTGG ATATAATGGT    780
TCGCAGCATG GGCCCAATAT CAGAGGTCGA TATGACCTAC TCGATGGACT GTTATTTCCG    840
CCAATCCTGG GTGGATAAAC GTCTCGCATT CGAGGGCGCC CAGGACACGC TGGCACTGAG    900
CGTCTCGATG TTGGCACGGA TTTGGAAGCC GGATACGTAC TTTTACAACG GCAAGCAGAG    960
CTATTTGCAC ACGATTACCA CGCCAAATAA GTTTGTGAGG ATCTATCAGA ACGGACGCGT   1020
GCTGTACTCC AGCCGGCTGA CAATTAAAGC CGGCTGCCCC ATGAATCTGG CCGATTTTCC   1080
AATGGATATA CAAAAGTGTC CTCTGAAATT CGGTTCATTT GGCTACACAA CGTCGGATGT   1140
CATCTACCGT TGGAACAAAG AAAGACCACC CGTCGCCATT GCCGAGGACA TGAAGCTGTC   1200
CCAATTCGAT TTGGTCGACT GTCCGGCTGG AAATTTAACG GACATTGTTT ACAAGGCGGC   1260
TGCTCCAAGA CCACAACGTC GCCCATTCAA CAACAAGGAT CCACCACGAC CCACCAGCAA   1320
GGTAATGACC ACTTTTGCCG GTCCCGCGGC AAAGAATCAG CATGTCCGCG GCACGGGACT   1380
CAAGCTGGAC AAAGGAGCCT TCGGTACCGG ACGGGATGCA ACTGGTGGCT CGGGGTCGAC   1440
CACCGGTCTA AGTGGCACTA TTACGCTGGA AACAAATCAT CCGTCGGAGT ACTCCATGTT   1500
GATGGTAAAC TTCCACCTGC AGCGTCACAT GGGCAACTTC CTGATCCAGG TGTACGGTCC   1560
CTGCTGCCTG CTGGTGGTCC TCAGTTGGGT GTCCTTCTGG CTGAACCGCG AGGCCACTGC   1620
TGATCGGGTT TCCCTCGGGA TCACTACCGT GCTGACGATG ACCTTTCTCG GACTGGAGGC   1680
TCGCACGGAT CTGCCCAAGG TGTCCTATCC CACGGCCCTG GACTTCTTCG TGTTCCTCTC   1740
GTTCGGCTTT ATCTTTGCCA CAATCCTGCA GTTTGCCGTG GTGCACTACT ACACCAAGTA   1800
CGGATCGGGG GAGTGCTATT TCATAATCGA GGAGCTGGAC TCGGAATCGG GGGAATCGGA   1860
GACGGAGCCA CTGACCTCGG ACTTTCGGGG CAGCACAGAG TCCAAGATCT ACGAAGTCAT   1920
TCCGCTGTCC ATGTGCGCTA TTAGCATGCC GCCGCCTCCC ACTCGGCTGG GCATGCTAAC   1980
CTCCAGGAAT CGGAGGCCCC GAAACAGGCG TCATGGTCTG TGGAGTATGA AGCTTCTGGG   2040
TCTCTTCGAC TGGCGGCGAA GAAGAAAGCC GCCACGTGCC GACTCCGACG AGGATGAGGA   2100
TGACGAGCAG ACGCAGCTAA GGGCCAACGA AGCACCGACC ACGTCTGCGG CAGCTGCGGC   2160
GGCACAAGCT GCTGCACAGG CTGCTCGGAT TAGTCCTCCA ACTGGAGGTC GCCGCAGGAT   2220
GTCCTACTAT CGACGCGAGG AGATGGAGGC CCGAAGGAAG GGCAAACGAA CGCCACAGTA   2280
CAATTCCGTG TCGAAGATCG ATCGCGCCTC GAGGATCGTC TTCCCACTGC TATTCATCCT   2340
TATCAACGTG TTCTATTGGT ACGGCTACTT GTCGAGGAGC TCAAGGATTT TGGCCAACAC   2400
GCCGGATGCG AGCACCTGAT GTTACCTTTT AGCAATTTAG ACAGGGTCCT CGAAGAAATC   2460
ATTAAGCGAT CGCCGGCGGC AAACTTACAA CTAAAGCTGA TGGAAAGCGA TGCATACGCA   2520
GAGTCGCGGA ATTTAAACAC TGCGATTCTA TAAAATCTTT GCACATGCAT CGTTTAAAAT   2580
CAGCTTAAGA CAAGGCGTGG GGGGAAAATC AGTTGGGGGA TTGGGAAAAG CAGGG         2635
```

( 2 ) INFORMATION FOR SEQ ID NO:4:

( i ) SEQUENCE CHARACTERISTICS:
        ( A ) LENGTH: 686 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:4:

```
Met Cys Thr Met Pro Ala Thr Arg Asp Ala Ser Gly Ser Gly Asp Ala
  1               5                  10                  15
Ser Thr Asp Leu Ile Ala Ala Arg Ser Leu Ser Ser His Gln Gly Gln
                 20                  25                  30
Arg Ser Asn Leu Arg Ile Phe Lys Leu Leu Ile Ser Cys Cys Leu Leu
             35                  40                  45
Met Leu Cys Ile Tyr Pro Asn Ala Trp Pro Trp Ser Ile Gly Pro Gly
         50                  55                  60
Ser Gly Pro Phe Ser Val Ser Ala Asp Ser Ile Lys Gly Arg Gly Asp
 65                  70                  75                  80
Thr His Arg Leu Gly Glu Met Gly Thr Ser Leu Ser Ser Ser Leu Pro
                 85                  90                  95
Ser Ser Trp Leu Thr Gln Ser Asn Asn His Ala Asn Ile Ser Glu Leu
            100                 105                 110
Leu Asp Asn Leu Leu Arg Gly Tyr Asp Asn Ser Ile Arg Pro Asp Phe
            115                 120                 125
Gly Gly Pro Pro Ala Thr Ile Glu Val Asp Ile Met Val Arg Ser Met
130                 135                 140
Gly Pro Ile Ser Glu Val Asp Met Thr Tyr Ser Met Asp Cys Tyr Phe
145                 150                 155                 160
Arg Gln Ser Trp Val Asp Lys Arg Leu Ala Phe Glu Gly Ala Gln Asp
                165                 170                 175
Thr Leu Ala Leu Ser Val Ser Met Leu Ala Arg Ile Trp Lys Pro Asp
                180                 185                 190
Thr Tyr Phe Tyr Asn Gly Lys Gln Ser Tyr Leu His Thr Ile Thr Thr
            195                 200                 205
Pro Asn Lys Phe Val Arg Ile Tyr Gln Asn Gly Arg Val Leu Tyr Ser
    210                 215                 220
Ser Arg Leu Thr Ile Lys Ala Gly Cys Pro Met Asn Leu Ala Asp Phe
225                 230                 235                 240
Pro Met Asp Ile Gln Lys Cys Pro Leu Lys Phe Gly Ser Phe Gly Tyr
                245                 250                 255
Thr Thr Ser Asp Val Ile Tyr Arg Trp Asn Lys Glu Arg Pro Pro Val
            260                 265                 270
Ala Ile Ala Glu Asp Met Lys Leu Ser Gln Phe Asp Leu Val Asp Cys
        275                 280                 285
Pro Ala Gly Asn Leu Thr Asp Ile Val Tyr Lys Ala Ala Ala Pro Arg
    290                 295                 300
Pro Gln Arg Arg Pro Phe Asn Asn Lys Asp Pro Arg Pro Thr Ser
305                 310                 315                 320
Lys Val Met Thr Thr Phe Ala Gly Pro Ala Ala Lys Asn Gln His Val
                325                 330                 335
Arg Gly Thr Gly Leu Lys Leu Asp Lys Gly Ala Phe Gly Thr Gly Arg
                340                 345                 350
Asp Ala Thr Gly Gly Ser Gly Ser Thr Thr Gly Leu Ser Gly Thr Ile
            355                 360                 365
Thr Leu Glu Thr Asn His Pro Ser Glu Tyr Ser Met Leu Met Val Asn
    370                 375                 380
Phe His Leu Gln Arg His Met Gly Asn Phe Leu Ile Gln Val Tyr Gly
```

```
385                           390                           395                           400
Pro  Cys  Cys  Leu  Leu  Val  Val  Leu  Ser  Trp  Val  Ser  Phe  Trp  Leu  Asn
                    405                      410                      415
Arg  Glu  Ala  Thr  Ala  Asp  Arg  Val  Ser  Leu  Gly  Ile  Thr  Thr  Val  Leu
                    420                      425                      430
Thr  Met  Thr  Phe  Leu  Gly  Leu  Glu  Ala  Arg  Thr  Asp  Leu  Pro  Lys  Val
               435                      440                      445
Ser  Tyr  Pro  Thr  Ala  Leu  Asp  Phe  Phe  Val  Phe  Leu  Ser  Phe  Gly  Phe
          450                      455                      460
Ile  Phe  Ala  Thr  Ile  Leu  Gln  Phe  Ala  Val  Val  His  Tyr  Tyr  Thr  Lys
465                           470                      475                      480
Tyr  Gly  Ser  Gly  Glu  Cys  Tyr  Phe  Ile  Ile  Glu  Glu  Leu  Asp  Ser  Glu
                    485                      490                      495
Ser  Gly  Glu  Ser  Glu  Thr  Glu  Pro  Leu  Thr  Ser  Asp  Phe  Arg  Gly  Ser
               500                      505                      510
Thr  Glu  Ser  Lys  Ile  Tyr  Glu  Val  Ile  Pro  Leu  Ser  Met  Cys  Ala  Ile
               515                      520                      525
Ser  Met  Pro  Pro  Pro  Pro  Thr  Arg  Leu  Gly  Met  Leu  Thr  Ser  Arg  Asn
          530                      535                      540
Arg  Arg  Pro  Arg  Asn  Arg  Arg  His  Gly  Leu  Trp  Ser  Met  Lys  Leu  Leu
545                           550                      555                      560
Gly  Leu  Phe  Asp  Trp  Arg  Arg  Arg  Lys  Pro  Pro  Arg  Ala  Asp  Ser
                    565                      570                      575
Asp  Glu  Asp  Glu  Asp  Asp  Glu  Gln  Thr  Gln  Leu  Arg  Ala  Asn  Glu  Ala
               580                      585                      590
Pro  Thr  Thr  Ser  Ala  Ala  Ala  Ala  Ala  Gln  Ala  Ala  Ala  Gln  Ala
          595                      600                      605
Ala  Arg  Ile  Ser  Pro  Pro  Thr  Gly  Gly  Arg  Arg  Arg  Met  Ser  Tyr  Tyr
     610                      615                      620
Arg  Arg  Glu  Glu  Met  Glu  Ala  Arg  Arg  Lys  Gly  Lys  Arg  Thr  Pro  Gln
625                      630                      635                      640
Tyr  Asn  Ser  Val  Ser  Lys  Ile  Asp  Arg  Ala  Ser  Arg  Ile  Val  Phe  Pro
               645                      650                      655
Leu  Leu  Phe  Ile  Leu  Ile  Asn  Val  Phe  Tyr  Trp  Tyr  Gly  Tyr  Leu  Ser
               660                      665                      670
Arg  Ser  Ser  Arg  Ile  Leu  Ala  Asn  Thr  Pro  Asp  Ala  Ser  Thr
          675                      680                      685
```

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

AAAACTCGAG GCACCACCAT GAG                        23

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

GCACTGTATG GATCCGTTTG TGG      23